US008969314B2

(12) United States Patent
Esau et al.

(10) Patent No.: US 8,969,314 B2
(45) Date of Patent: Mar. 3, 2015

(54) METHODS FOR USE IN MODULATING MIR-122A

(75) Inventors: Christine Esau, La Jolla, CA (US); Sanjay Bhanot, Carlsbad, CA (US)

(73) Assignee: Regulus Therapeutics, Inc., San Diego, CA (US)

( * ) Notice: Subject to any disclaimer, the term of this patent is extended or adjusted under 35 U.S.C. 154(b) by 0 days.

(21) Appl. No.: 11/513,102

(22) Filed: Aug. 29, 2006

(65) Prior Publication Data

US 2007/0049547 A1    Mar. 1, 2007

Related U.S. Application Data

(60) Provisional application No. 60/712,211, filed on Aug. 29, 2005, provisional application No. 60/731,377, filed on Oct. 28, 2005, provisional application No. 60/771,592, filed on Feb. 7, 2006.

(51) Int. Cl.
*C12N 15/11* (2006.01)
*C12N 15/113* (2010.01)

(52) U.S. Cl.
CPC .......... *C12N 15/113* (2013.01); *C12N 2310/11* (2013.01); *C12N 2310/113* (2013.01); *C12N 2310/315* (2013.01); *C12N 2310/321* (2013.01); *C12N 2310/3231* (2013.01); *C12N 2310/3341* (2013.01); *C12N 2310/341* (2013.01); *C12N 2310/345* (2013.01); *C12N 2310/346* (2013.01)
USPC ..................................................... 514/44 A

(58) Field of Classification Search
USPC .......... 514/44, 81, 12; 435/6, 375; 800/14, 18
See application file for complete search history.

(56) References Cited

U.S. PATENT DOCUMENTS

| | | | | |
|---|---|---|---|---|
| 8,541,385 B2 * | 9/2013 | Stoffel et al. | ............... | 514/44 A |
| 2004/0019026 A1 * | 1/2004 | Schwartz | ...................... | 514/177 |
| 2004/0204356 A1 * | 10/2004 | Guenzler-Pukall et al. | ..... | 514/12 |
| 2004/0214325 A1 * | 10/2004 | Crooke et al. | ................. | 435/375 |
| 2005/0261218 A1 * | 11/2005 | Esau et al. | ...................... | 514/44 |
| 2006/0035858 A1 * | 2/2006 | Geary et al. | ..................... | 514/44 |
| 2006/0058266 A1 * | 3/2006 | Manoharan et al. | ............ | 514/81 |
| 2006/0185027 A1 * | 8/2006 | Bartel et al. | ..................... | 800/14 |
| 2006/0265771 A1 * | 11/2006 | Lewis et al. | ...................... | 800/18 |
| 2007/0123482 A1 | 5/2007 | Stoffel et al. | | |

FOREIGN PATENT DOCUMENTS

| | | |
|---|---|---|
| WO | 01/25248 A2 | 4/2001 |
| WO | 03/011887 | 2/2003 |
| WO | 03/029459 | 4/2003 |
| WO | 03/029459 A2 | 4/2003 |
| WO | 2004052284 A2 * | 6/2004 |
| WO | WO 2005013901 A2 * | 2/2005 |
| WO | 2005/107816 | 11/2005 |
| WO | 2007/027775 A2 | 3/2007 |
| WO | 2007/027894 A2 | 3/2007 |
| WO | 2007/112753 | 10/2007 |
| WO | 2007/112754 | 10/2007 |

OTHER PUBLICATIONS

Tomomura et al., Proto-oncogene c-jun and c-fos messenger RNAs increase in the liver of carnitine-deficient juvenile visceral steatosis (jvs) mice, Oct. 1992, FEBS Letters, vol. 311, pp. 63-66.*
Hittel et al., Proteome analysis of skeletal muscle from obese and morbidly obese women, May 2005, Diabetes, vol. 54, pp. 1283-1288.*
Marchesini et al., Nonalcoholic fatty liver disease: A feature of the metabolic syndrome, 2001, Diabetes, vol. 50, pp. 1844-1850.*
Dipak K. Das, Cardioprotection with high-density lipoproteins: fact or fiction? 2003, Circulation Research, vol. 92, pp. 258-260.*
Sugano et al., Changes in plasma lipoprotein cholesterol levels by antisense oligodeoxynucleotides against cholesteryl ester transfer protein in cholesterol-fed rabbits, 1996, The Journal of Biological Chemistry, vol. 271, pp. 19080-19083.*
David M. Nathan, Initial management of glycemia in Type 2 diabetes mellitus, 2002, The New England Journal of Medicine, vol. 347, pp. 1342-1349.*
Lagos-Quintana, M. et al., "Identification of Tissue-Specific MicroRNAs from Mouse," Curr. Biol, (2002) 12 (9):735-739.
Wahlestedt, et al., Potent and nontoxic antisense oligonucleotides containing locked nucleic acids, National Academy of Science, vol. 97, No. 10, pp. 5633-5638, 2000.
Esau, et al., miR-122 regulation of lipid metabolism revealed by in vivo antisense targetting, Cell Metabolism, vol. 3, No. 2, pp. 87-98, 2006.
Chang J. et al., "miR-122, a Mammalian Liver-Specific MicroRNA is Processed from her mRNA and May Downregulate the High Affinity Cationic Amino Acid Transporter CAT-1," RNA Biology vol. 1, pp. 106-113, 2004.
Jopling, et al., Modulation of Hepatitis C Virus RNA Abundance by a Liver-Specific MicroRNA, Science, vol. 309, pp. 1577-1581, 2005.
Krutzfeldt, et al., Silencing fo MicroRNAs in Vivo with Antagmirs, Nature, vol. 438, pp. 685-689, 2005.

(Continued)

*Primary Examiner* — Dana Shin
(74) *Attorney, Agent, or Firm* — Frances R. Putkey; Casimir Jones, S.C.

(57) ABSTRACT

Methods are provided for the treatment of cardiovascular or metabolic diseases characterized by elevated serum total cholesterol, elevated serum LDL-cholesterol, or elevated serum triglycerides, through the administration of an oligomeric compound which modulates the levels or activity of miR-122a. Further provided are methods for reducing hepatic steatosis or liver tissue triglyceride accumulation through the administration of an oligomeric compound which modulates the levels or activity of miR-122a. Such methods employ oligomeric compounds which hybridize with or sterically interfere with nucleic acid molecules comprising or encoding miR-122a. Such oligomeric compounds may include one or more modifications thereon, which may improve the activity, stability, or nuclease resistance of the oligomeric compound. These modified oligomeric compounds are used as single compounds or in compositions, including pharmaceutical compositions, to modulate or mimic the targeted nucleic acid comprising or encoding miR-122a.

37 Claims, No Drawings

(56) References Cited

OTHER PUBLICATIONS

International Search Report for International application PCT/US2006/033866 dated Jun. 11, 2007.
International Search Report for International application PCT/US2006/034032 dated Apr. 5, 2007.
Communication pursuant to Article 94(3) EPC for EP Application No. 06813949.2, dated Jul. 31, 2008.
Communication pursuant to Article 94(3) EPC for EP Application No. 06802706.9, dated Jul. 14, 2008.
Naguibneva, I. et al; "An LNA-based-loss-of-function assay for micro-RNAs"; Biomedicine & Pharmacotherapy; 60: 633-638 (2006).
Partial European Search Report, mailed May 3, 2011, in EP10179177.0.
Valoczi, A., et al, Sensitive and specific detection of microRNAs by norther blot analysis using LNA-modified oligonucleotide probes, Nucleic Acids Research (2004), 32(22): e175.
Davis, S., et al, Improved targeting of miRNA with antisense oligonucleotides, Nucleic Acids Research (2006), 34(8): 2294-2304.
Krützfedt, J., et al, Specificity, duplex degradation and subcellular localization of antagomirs. Nucleic Acids Research (2007), 35(9): 2885-2892.
Bhat, B., et al. Nucleic Acids Symposium Series (2008), 52: 69.
Esau, C., et al, MicroRNA-143 Regulated Adipocyte Differentiation, J. Biological Chemistry (2004), 279(50): 52361-52365.
U.S. Appl. No. 10/909,125 (D1 US Equivalent)—File history response filed by the Patent Proprietor on Apr. 8, 2009.
Declaration of Dr. Susanna Obad (opponent's declaration), dated Sep. 27, 2011.
Communication of a notice of opposition and Acknowledgement of receipt from the European Patent Office, mailed Oct. 10, 2011, in European Patent No, 1931782 B1.
Opposition against European Patent No. 1931782 B1 filed Oct. 4, 2011.
Izzo, Human aldolase A gene, Eur. J. Biochem., (1988), 174, 569-578.
Siperstein et al., "Role of Glycolysis in Fatty Acid and Cholesterol Synthesis in Normal and Diabetic Rats," Science, 126(3281):1012-1013, (1957).
Binder et al., Replication Vesicles are Load- and Choke-Points in the Hepatitis C Virus Lifecycle, PLoS Pathogens, 2013, 9(8):e1003561, 21 pages.
BusinessWire, BioCryst Announces Promising Results from Preclinical Studies of BCX5191 for Hepatitis C, Feb. 15, 2012, 4 pages.
Bukh et al., Mutations that permit efficient replication of hepatitis C virus RNA in Huh-7 cells prevent productive prelication in chimpanzees, PNAS, 2002, 99(22):14416-14421.
Elvidge, Troubled BioCryst dumps HCV preclinical program, FierceBiotech Research, Jan. 29, 2013, 3 pages.
Janssen et al., Treatment of HCV Infection by Targeting MicroRNA, NEJM, 2013, 368:1685-1694.
Lanford et al., Antiviral Effect and Virus-Host Interactions in Response to Alpha Interferon, Gamma Interferon, Poly(I)-Poly(C), Tumor Necrosis Factor Alpha, and Ribavirin in Hepatitis C Virus Subgenomic Replicons, J Virol, 2003, 77 (2):1092-1104.
Declaration of Morten Lindow, dated Dec. 11, 2013, 2 pages.
Regulus Therapeutics Inc., Regulus Reports Second Quarter 2013 Financial Results and Recent Highlights, Aug. 13, 2013, 4 pages.
Sumpter et al., Regulating Intracellular Antiviral Defense and Permissiveness to Hepatitis C Virus RNA Replication through a Cellular RNA Helicase, RIG-I, J Virol, 2005, 79(5):2689-2699.
Opponent's Further Submissions filed in EP1747023, dated Dec. 20, 2013, with Brief Communication from the European Patent Office, dated Jan. 9, 2014, 18 pages.
Summons to attend oral proceedings pursuant to Rule 115(1) EPC mailed Feb. 14, 2014, for EP Patent No. 1 931 782, 21 pages.
Fu et al., "Identification of human fetal liver miRNAs by a novel method," FEBS Lett, 2005, 579(17):3849-3854.
BBC—Health: Cholesterol, www.bbc.co.uk/physical_health/conditions/cholesterol1.shtml, retrieved Jan. 9, 2011, 3 pages.
Graphical representation of the data in Table 9 of opposed patent, filed Oct. 4, 2011 in opposition proceedings for EP1931782, 3 pages.
Stryer, Biochemistry, 2nd edition, 1981, W.H. Freeman publisher, Freeman, NY, pp. 266-268.
Proprietor's Response to Opposition of EP Patent 1931782, filed Jul. 19, 2012, with the European Patent Office, 15 pages.
Proprietor's amended claims filed Jul. 19, 2012, in the Opposition proceedings of EP Patent 1931782, 2 pages.
U.S. Appl. No. 60/796,813, filed May 1, 2006.
Declaration of Dr. Susanna Obad, dated Sep. 27, 2011, 4 pages.
Stenvang & Kauppinen, "MicroRNAs as targets for antisense-based therapeutics," Expert Opin. Biol. Ther., 2008, 8(1):59-81.
Stenvang et al., "Inhibition of microRNA function by antimiR oligonucleotides," Silence, 2012, 3:1, 17 pages.
Chan et al., "MicroRNA-21 is an Antiapoptotic Factor in Human Glioglastoma Cells," Cancer Res, 2005, 65(14):6029-6033.
Cheng et al., "Antisense inhibition of human miRNAs and indications for an involvement of miRNA in cell growth and apoptosis," Nucleic Acid Res., 2005, 33(4)1290-1297.
Levin, "A review of issues in the pharmacokinetics and toxicology of phosphorothioate antisense oligonucleotides," Biochimica et Biophysica Acta, 1999, 1489:69-84.
Boutla, A., et al., Developmental defects by antisense-mediated inactivation of micro-RNAs 2 and 13 in *Drosophila* and the identification of putative target genes, Nucleic Acids Res., 2003;31(17):4973-80.
Hutvagner, G., et al., Sequence-Specific inhibition of small RNA function, PLoS Biol., 2004;2(4):0001-0011.
Meister, G., et al., Sequence-specific inhibition of microRNA- and siRNA-induced RNA silencing, RNA. Mar. 2004;10(3):544-50.

* cited by examiner

SEQUENCE LISTING

```
<160> NUMBER OF SEQ ID NOS: 30

<210> SEQ ID NO 1
<211> LENGTH: 22
<212> TYPE: DNA
<213> ORGANISM: Artificial Sequence
<220> FEATURE:
<223> OTHER INFORMATION: Synthetic Antisense Oligonucleotide

<400> SEQUENCE: 1
caaacaccat tgtcacactc ca                                            22

<210> SEQ ID NO 2
<211> LENGTH: 23
<212> TYPE: DNA
<213> ORGANISM: Artificial Sequence
<220> FEATURE:
<223> OTHER INFORMATION: Synthetic Antisense Oligonucleotide

<400> SEQUENCE: 2
acaaacacca ttgtcacact cca                                           23

<210> SEQ ID NO 3
<211> LENGTH: 23
<212> TYPE: RNA
<213> ORGANISM: H. sapiens

<400> SEQUENCE: 3
uggaguguga caauguguu ugu                                            23

<210> SEQ ID NO 4
<211> LENGTH: 22
<212> TYPE: RNA
<213> ORGANISM: H. sapiens

<400> SEQUENCE: 4
uggaguguga caauguguu ug                                             22

<210> SEQ ID NO 5
<211> LENGTH: 110
<212> TYPE: RNA
<213> ORGANISM: H. sapiens

<400> SEQUENCE: 5
uggcuacaga guuuccuuag cagagcugug gaguggaca augguguuug ugcuaaacu     60 aucaaacgcc auuaucacac uaaauagcua cugcuaggca auccuuccu              110

<210> SEQ ID NO 6
<211> LENGTH: 81
<212> TYPE: RNA
<213> ORGANISM: M. musculus

<400> SEQUENCE: 6
uuccuuagca gagcugugga gugugacaau ggguguugug uccaaaccau caaacgccau   60
uaucacacua aauagcuacu g                                             81

<210> SEQ ID NO 7
<211> LENGTH: 80
<212> TYPE: RNA
<213> ORGANISM: R. norvegicus

<400> SEQUENCE: 7
uccuuagcag agcucuggag ugugacaaug guguugugu ccaaaacauc aaacgccauc   60
```

-continued aucacacuaa acagcuacug                                         80

<210> SEQ ID NO 8
<211> LENGTH: 23
<212> TYPE: DNA
<213> ORGANISM: Artificial Sequence
<220> FEATURE:
<223> OTHER INFORMATION: Synthetic Antisense Oligonucleotide

<400> SEQUENCE: 8
aaacaccatt gtcacactcc aca                                     23

<210> SEQ ID NO 9
<211> LENGTH: 26
<212> TYPE: DNA
<213> ORGANISM: Artificial Sequence
<220> FEATURE:
<223> OTHER INFORMATION: Synthetic Antisense Oligonucleotide

<400> SEQUENCE: 9
gctatttagt gtgataatgg cgtttg                                  26

<210> SEQ ID NO 10
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 10
gggaaggatt gcctagcagt                                         20

<210> SEQ ID NO 11
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 11
tttgatagtt tagacacaaa                                         20

<210> SEQ ID NO 12
<211> LENGTH: 21
<212> TYPE: DNA
<213> ORGANISM: Artificial Sequence
<220> FEATURE:
<223> OTHER INFORMATION: Synthetic Antisense Oligonucleotide

<400> SEQUENCE: 12
gtttgatagt ttagacacaa a                                       21

<210> SEQ ID NO 13
<211> LENGTH: 21
<212> TYPE: DNA
<213> ORGANISM: Artificial Sequence
<220> FEATURE:
<223> OTHER INFORMATION: Synthetic Antisense Oligonucleotide

<400> SEQUENCE: 13
acaaacacca ttgtcacact c                                       21

<210> SEQ ID NO 14
<211> LENGTH: 19
<212> TYPE: DNA

```
<213> ORGANISM: Artificial Sequence
<220> FEATURE:
<223> OTHER INFORMATION: Synthetic Antisense Oligonucleotide

<400> SEQUENCE: 14
acaaacacca ttgtcacac                                                   19

<210> SEQ ID NO 15
<211> LENGTH: 17
<212> TYPE: DNA
<213> ORGANISM: Artificial Sequence
<220> FEATURE:
<223> OTHER INFORMATION: Synthetic Antisense Oligonucleotide

<400> SEQUENCE: 15
acaaacacca ttgtcac                                                     17

<210> SEQ ID NO 16
<211> LENGTH: 21
<212> TYPE: DNA
<213> ORGANISM: Artificial Sequence
<220> FEATURE:
<223> OTHER INFORMATION: Synthetic Antisense Oligonucleotide

<400> SEQUENCE: 16
aaacaccatt gtcacactcc a                                                21

<210> SEQ ID NO 17
<211> LENGTH: 19
<212> TYPE: DNA
<213> ORGANISM: Artificial Sequence
<220> FEATURE:
<223> OTHER INFORMATION: Synthetic Antisense Oligonucleotide

<400> SEQUENCE: 17
acaccattgt cacactcca                                                   19

<210> SEQ ID NO 18
<211> LENGTH: 17
<212> TYPE: DNA
<213> ORGANISM: Artificial Sequence
<220> FEATURE:
<223> OTHER INFORMATION: Synthetic Antisense Oligonucleotide

<400> SEQUENCE: 18
accattgtca cactcca                                                     17

<210> SEQ ID NO 19
<211> LENGTH: 23
<212> TYPE: DNA
<213> ORGANISM: Artificial Sequence
<220> FEATURE:
<223> OTHER INFORMATION: Synthetic Antisense Oligonucleotide

<400> SEQUENCE: 19
acatacacca ttgtcacagt cca                                              23

<210> SEQ ID NO 20
<211> LENGTH: 23
<212> TYPE: DNA
<213> ORGANISM: Artificial Sequence
<220> FEATURE:
<223> OTHER INFORMATION: Synthetic Antisense Oligonucleotide

<400> SEQUENCE: 20
acatacacca ttgtcacact cca                                              23
```

```
<210> SEQ ID NO 21
<211> LENGTH: 23
<212> TYPE: DNA
<213> ORGANISM: Artificial Sequence
<220> FEATURE:
<223> OTHER INFORMATION: Synthetic Antisense Oligonucleotide

<400> SEQUENCE: 21
acatacacca ttctcacagt cca                                             23

<210> SEQ ID NO 22
<211> LENGTH: 23
<212> TYPE: DNA
<213> ORGANISM: Artificial Sequence
<220> FEATURE:
<223> OTHER INFORMATION: Synthetic Antisense Oligonucleotide

<400> SEQUENCE: 22
acatacacct ttctcacagt cca                                             23

<210> SEQ ID NO 23
<211> LENGTH: 23
<212> TYPE: DNA
<213> ORGANISM: Artificial Sequence
<220> FEATURE:
<223> OTHER INFORMATION: Synthetic Antisense Oligonucleotide

<400> SEQUENCE: 23
acatacacct ttctcagagt cca                                             23

<210> SEQ ID NO 24
<211> LENGTH: 23
<212> TYPE: DNA
<213> ORGANISM: Artificial Sequence
<220> FEATURE:
<223> OTHER INFORMATION: Synthetic Antisense Oligonucleotide

<400> SEQUENCE: 24
acatactcct ttctcagagt cca                                             23

<210> SEQ ID NO 25
<211> LENGTH: 23
<212> TYPE: RNA
<213> ORGANISM: Artificial Sequence
<220> FEATURE:
<223> OTHER INFORMATION: Synthetic Antisense Oligonucleotide

<400> SEQUENCE: 25
aaacaccauu gucacacucc aua                                             23

<210> SEQ ID NO 26
<211> LENGTH: 23
<212> TYPE: RNA
<213> ORGANISM: Artificial Sequence
<220> FEATURE:
<223> OTHER INFORMATION: Synthetic Antisense Oligonucleotide

<400> SEQUENCE: 26
ugcacagaga caaugguguu ugu                                             23

<210> SEQ ID NO 27
<211> LENGTH: 23
<212> TYPE: RNA
<213> ORGANISM: Artificial Sequence
<220> FEATURE:
```

-continued

```
<223> OTHER INFORMATION: Synthetic Antisense Oligonucleotide

<400> SEQUENCE: 27
aaacaccauu gucucugugc aua                                              23

<210> SEQ ID NO 28
<211> LENGTH: 23
<212> TYPE: RNA
<213> ORGANISM: Artificial Sequence
<220> FEATURE:
<223> OTHER INFORMATION: Synthetic Antisense Oligonucleotide

<400> SEQUENCE: 28
uggaguguga cauugcagua gug                                              23

<210> SEQ ID NO 29
<211> LENGTH: 23
<212> TYPE: RNA
<213> ORGANISM: Artificial Sequence
<220> FEATURE:
<223> OTHER INFORMATION: Synthetic Antisense Oligonucleotide

<400> SEQUENCE: 29
auacugcaau gucacacucc aua                                              23

<210> SEQ ID NO 30
<211> LENGTH: 22
<212> TYPE: DNA
<213> ORGANISM: Artificial Sequence
<220> FEATURE:
<223> OTHER INFORMATION: Synthetic Antisense Oligonucleotide

<400> SEQUENCE: 30
ccttccctga aggttcctcc tt                                               22
```

METHODS FOR USE IN MODULATING MIR-122A

CROSS-REFERENCE TO RELATED APPLICATIONS

This application claims priority under 35 U.S.C. § 119(e) to U.S. Provisional Application Ser. No. 60/712,211 filed Aug. 29, 2005, U.S. Provisional Application Ser. No. 60/731, 377 filed Oct. 28, 2005, and U.S. Provisional Application Ser. No. 60/771,592, filed Feb. 7, 2006, each of which is incorporated herein by reference in its entirety.

This application is related to U.S. application Ser. No. 10/909,125 filed Jul. 30, 2004 which claims priority to U.S. provisional application Ser. No. 60/492,056 filed Jul. 31, 2003, Ser. No. 60/516,303 filed Oct. 31, 2003, Ser. No. 60/531,596 filed Dec. 19, 2003, and Ser. No. 60/562,417 filed Apr. 14, 2004, each of which is incorporated herein by reference in its entirety.

FIELD OF THE INVENTION

The present invention provides methods for the modulation of small non-coding RNAs, in particular miR-122a. Methods are provided for the treatment of cardiovascular or metabolic diseases characterized by elevated serum total cholesterol, elevated serum LDL-cholesterol, or elevated serum triglycerides, through the administration of an antisense compound which inhibits the levels or activity of miR-122a. Further provided are methods for reducing hepatic steatosis or liver tissue triglyceride accumulation through the administration of an antisense compound which inhibits the levels or activity of miR-122a. Such methods employ antisense compounds which hybridize with or sterically interfere with nucleic acid molecules comprising or encoding miR-122a. Such antisense compounds may include one or more modifications thereon, which may improve the activity, stability, or nuclease resistance of the antisense compound. These modified antisense compounds are used as single compounds or in compositions, including pharmaceutical compositions, to inhibit miR-122a.

BACKGROUND OF THE INVENTION

MicroRNAs (miRNAs) are small (approximately 21-24 nucleotides in length, these are also known as "mature" miRNA), non-coding RNA molecules encoded in the genomes of plants and animals. These highly conserved, endogenously expressed RNAs are believed to regulate the expression of genes by binding to the 3'-untranslated regions (3'-UTR) of specific mRNAs. miRNAs may act as key regulators of cellular processes such as cell proliferation, cell death (apoptosis), metabolism, and cell differentiation. On a larger scale, miRNA expression has been implicated in early development, brain development, disease progression (such as cancers and viral infections). There is speculation that in higher eukaryotes, the role of mRNAs in regulating gene expression could be as important as that of transcription factors. More than 200 different mRNAs have been identified in plants and animals (Ambros et al., Curr. Biol., 2003, 13, 807-818). Mature mRNAs appear to originate from long endogenous primary mRNA transcripts (also known as pri-miRNAs, pri-miRs, pri-miRs or pri-pre-mRNAs) that are often hundreds of nucleotides in length (Lee, et al., EMBO J., 2002, 21(17), 4663-4670).

In mammals, only a few mRNAs have been assigned any function, although they are predicted to regulate a large percentage of genes, with estimates based on bioinformatic target prediction ranging as high as 30% (Lewis et al., 2005). Based on the early studies in invertebrates, miRNAs are expected to have similar roles in developmental regulation and cell differentiation in mammals, and roles for mRNAs in cardiogenesis (Zhao et al., 2005) and lymphocyte development (Chen et al., 2004) have been demonstrated. Several studies have also found a strong connection between mRNA and human cancer, including a report that mRNA genes are often found in genomic regions linked to cancer (Calin et al., 2004; McManus, 2003) and a study correlating mRNA expression profiles with developmental lineage and differentiation state of tumors (Lu et al., 2005). A potential role for mRNAs in metabolic pathways has been suggested by studies implicating mRNAs in regulation of adipocyte differentiation (Esau et al., 2004) and glucose-stimulated insulin secretion from pancreatic islet cells (Poy et al., 2004). miR-122a is expressed in the developing liver (Chang et al., 2004) and at high levels in the adult liver, where it makes up 70% of all mRNA (Chang et al., 2004; LagosQuintana et al., 2002). It is one of many tissue-specific microRNAs thought to be important for establishing patterns of gene expression which may be responsible for maintaining the differentiated state of a tissue (Lagos-Quintana et al., 2002; Lim et al., 2005). miR-122a was also reported to enhance replication of HCV through a novel mechanism which is not yet understood, making it also a potential therapeutic target for HCV infection (Jopling et al., 2005).

It is described herein that the modulation of miR-122a is an attractive approach for diseases and conditions characterized by elevated serum cholesterol, elevated serum triglycerides, or hepatic steatosis. The present invention therefore provides antisense compounds and methods useful for modulating miR-122a, to achieve clinically desirable changes in cholesterol and lipid profiles in animals.

SUMMARY OF THE INVENTION

The present invention provides methods of lowering a serum indicator of cardiovascular disease risk, which include elevated serum total cholesterol elevated serum LDL-cholesterol, and elevated serum triglyceride levels, comprising selecting an animal having an elevate serum indicator of cardiovascular disease, and administering to the animal an antisense compound targeted to miR-122a.

The present invention provides methods of lowering serum cholesterol in an animal comprising selecting an animal having elevated serum cholesterol levels, and then administering to the animal a therapeutically effective amount of an antisense compound essentially complementary to a miR-122a nucleic acid. The serum cholesterol levels may be total serum cholesterol levels or serum LDL-cholesterol levels.

The present invention further provides a method of lowering triglyceride levels in an animal comprising selecting an animal having elevated triglyceride levels, and then administering to the animal a therapeutically effective amount of an antisense compound essentially complementary to a miR-122a nucleic acid. The triglyceride levels may be serum triglyceride levels or liver tissue triglyceride levels.

Further provided is a method of lowering serum lipoproteins in an animal comprising selecting an animal having elevated serum lipoproteins and administering to the animal a therapeutically effective amount of an antisense compound essentially complementary to a miR-122a nucleic acid. The serum lipoprotein may be apolipoprotein B1-100.

The present invention provides methods of reducing hepatic steatosis in an animal comprising selecting an animal having hepatic steatosis and administering to the animal a therapeutically effective amount of an antisense compound essentially complementary to a miR-122a nucleic acid. The hepatic steatosis may be steatohepatitis or non-alcoholic steatohepatitis.

Additionally provides are methods of reducing triglyceride accumulation in the liver of an animal comprising administering to the animal a therapeutically effective amount of an antisense compound essentially complementary to a miR-122a nucleic acid.

The present invention provides methods of modulating a metabolic pathway in an animal, comprising administering to an animal a therapeutically effective amount of an antisense compound essentially complementary to a miR-122a nucleic acid. The metabolic pathway is selected from lipogenesis, fatty acid oxidation, fatty acid synthesis rate, or sterol synthesis. The methods provided reduce lipogenesis, reduce fatty acid synthesis rate, reduce sterol synthesis, or increase fatty acid oxidation.

Further provided is a method of improving hepatic function in an animal comprising contacting an animal with a therapeutically effective amount of an antisense compound essentially complementary to a miR-122a nucleic acid. The improvement in hepatic function is measured by measuring the levels of plasma transaminases, wherein a decrease in plasma transaminases indicate an improvement in hepatic function.

Also provided are methods of treating a cardiovacular or metabolic disease or disorder selected from diabetes, obesity, hyperlipidemia, hypercholesterolemia, hypertriglyceridemia, hyperfattyacidemia, nonalcoholic fatty liver disease, non alcoholic steatohepatitis, or metabolic syndrome. The animal is treated through the administration of a therapeutically effective amount of an antisense compound essentially complementary to a miR-122a nucleic acid.

In any of the aforementioned methods, the antisense compound is essentially fully complementary to a miR-122a target nucleic acid. Alternatively, the antisense compound is fully complementary to a miR-122a target nucleic acid. The antisense compound comprises at plurality of sugar modified nucleosides. The plurality of sugar modified nucleosides may, in some embodiments comprise 2 distinct sugar modifications. In certain embodiments the sugar modified nucleosides may further comprise at least one bicyclic sugar modification. In some embodiments, each nucleoside of the plurality of sugar modified nucleosides may comprise a 2'-MOE sugar modification. The antisense compound may comprise at least one phosphorothioate internucleoside linkage. The antisense compound may further comprise a least one 5-methylcytosine.

An antisense compound comprising the nucleobase sequence SEQ ID NO: 1 may be used in any of the aforementioned methods. Further, an antisense compound consisting of the nucleobase sequence of SEQ ID NO: 2. may be used in any of the aforementioned methods. The antisense compound may comprise ISIS 327895 or ISIS 387574.

The present invention provides the use of an antisense compound essentially fully complementary to a miR-122 nucleic acid for the preparation of a medicament for lowering a serum indicator of cardiovascular disease risk wherein the serum indicator of cardiovascular disease risk is selected from elevated serum cholesterol levels, elevated serum triglyceride levels, or elevated lipoprotein levels. The elevated serum cholesterol may be elevated LDL-cholesterol, or elevated serum total cholesterol. The elevated serum lipoprotein may be elevated serum ApoB-100.

The present invention further provides the use of an antisense compound essentially fully complementary to a miR-122a nucleic acid for the preparation of a medicament for reducing hepatic steatosis. The hepatic steatosis is steatohepatitis or non-alcoholic steatohepatitis.

The present invention additionally provides the use of an antisense compound essentially fully complementary to a miR-122a nucleic acid in the preparation of a medicament to treat a disease or disorder selected from diabetes, obesity, hyperlipidemia, hypercholesterolemia, hypertriglyceridemia, hyperfattyacidemia, nonalcoholic fatty liver disease, non alcoholic steatohepatitis, or metabolic syndrome.

In any of the aforementioned uses, the antisense compound used in the preparation of the medicament is 21 to 23 nucleosides in length. Further, the antisense compound may be fully complementary to a miR-122a nucleic acid. Additionally, the antisense compound may comprise a plurality of 2'-sugar modified nucleosides. The antisense compound may further comprise at least one bicyclic sugar modified nucleoside. Additionally, the antisense compound comprises the nucleobase sequence of SEQ ID NO: 1. Alternatively, the antisense compound consists of the nucleobase sequence of SEQ ID NO: 2. The antisense compound used in the preparation of the medicament may be uniformly comprised of 2'-MOE sugar modified nucleosides. The antisense compound may further comprise at least one phosphorothioate internucleoside linkage. The antisense compound may additionally comprise at least one 5-methylcytosine.

DETAILED DESCRIPTION OF THE INVENTION

It has been found that antisense inhibition of mir-122a resulted in clinically desirable improvements in cholesterol and lipid profiles in animal models of hyperlipidemia and obesity. Accordingly, the present invention provides antisense compounds that hybridize to and inhibit the levels, activity or expression of a miR-122a target nucleic acid, i.e. the antisense compounds are targeted to a miR-122a nucleic acid. The antisense compounds are chemically modified to enhance stability and affinity for a miR-122a nucleic acid. In one embodiment, the antisense compounds comprise a plurality of sugar modified nucleosides. In another embodiment, the plurality of sugar modified nucleosides comprises at least 2 distinct sugar modified nucleosides. In some embodiment, the plurality of sugar modified nucleosides comprises at least one bicyclic sugar modified nucleoside. In an additional embodiment, the antisense compounds are uniformly modified such that each nucleoside bears a 2'-MOE modification. In some embodiments, the antisense compound comprises the nucleobase sequence CAAACACCATTGTCACACTCCA (SEQ ID NO: 1). In preferred embodiments, the antisense compound has the nucleobase sequence ACAAACACCATTGTCACACTCCA (SEQ ID NO: 2). In further embodiments, the antisense compound is ISIS 327895 or ISIS 387574.

The present invention provides methods of administering antisense compounds targeted to a miR-122a nucleic acid to an animal to lower serum cholesterol, serum LDL-cholesterol, or serum triglycerides. The present invention also provides methods of reducing hepatic steatosis, liver triglyceride levels and liver weights. Additionally provided are methods of improving liver function, which is evaluated, for example, by decreases in serum transaminases. Also provided are methods of modulating the expression of a miR-122a mRNA target, such as ALDO A. The antisense compounds of the invention are also used for the modulation of metabolic pathways, for example, to lower sterol synthesis, to reduce lipogenesis, reduce fatty acid synthesis rate, reduce sterol synthesis, or increase fatty acid oxidation.

The present invention provides methods for the treatment of diseases or conditions characterized by elevated serum cholesterol levels, elevated serum triglyercide levels, or elevated liver triglyceride levels. These diseases or conditions may be further characterized by compromised liver function as measured by increases in plasma transaminases.

In one embodiment, the methods provided herein are useful for the treatment of diseases or conditions including hyperlipidemia, hypercholesterolemia, hypertriglyceridemia, or hyperfattyacidemia. In a further embodiment, the methods are useful for the treatment of hepatic steatosis or non-alcholic fatty liver disease. In some embodiments, the steatosis is steatohepatitis. In further embodiments, the steatotis is NASH. A further embodiment includes the use of the methods provided for the treatment of metabolic sydrome. In one embodiment, the methods comprise the administration of antisense compounds targeted to miR-122a to an animal, particularly a human, having or susceptible to a disease or condition including, but not limited to, hyperlipidemia, hypercholesterolemia, hypertriglyceridemia, hyperfattyacidemia, steatohepatitis, non-alcoholic steatohepatitis, non-alcoholic fatty liver disease, or metabolic syndrome. In another embodiment, the disease or condition is a cardiovascular disease or a metabolic disease. In one aspect, the disease or condition is treated or ameliorated through the administration to the human of a therapeutically effective amount of an antisense compound of the invention. Alternatively, the onset of the disease or condition is delayed or prevented through the administration to the human of a prophylactically effective amount of an antisense compound of the invention.

Embodiments described herein additionally relate to the use of an antisense compound targeted to a miR-122a nucleic acid in the preparation of a medicament for the treatment of a disease or condition including hyperlipidemia, hypercholesterolemia, hypertriglyceridemia, or hyperfattyacidemia. In further embodiments, the medicament is used for the treatment of hepatic steatosis, which may be steatohepatitis or NASH, or non-alcoholic fatty liver disease. In an additional embodiment, the medicament is used for the treatment of metabolic syndrome. In a further embodiment, the medicament is used for the improvement of liver function. The medicament may, in some embodiments, be administered parenterally, which includes intravenous administration and subcutaneous administration.

Antisense compounds of the invention modulate the levels, activity, or expression of a miR-122a nucleic acid by hybridizing to a miR-122a nucleic acid (i.e., antisense compounds target the miR-122a nucleic acids) and thereby interfering with its endogenous function. The hybridization of an antisense compound targeting a miR-122a nucleic acid may trigger the degradation, cleavage, and/or sequestration of the miR-122a nucleic acid, each of which interferes with the activity of the miR-122a nucleic acid. The hybridization of an antisense compound targeting miR-122a may also interfere with the activity of miR-122a by steric occlusion. The inhibition of miR-122a levels, activity or expression that results from an antisense compound hybridizing to a miR-122a nucleic acid is referred to as "antisense inhibition."

In the context of the present invention, "modulation of a miR-122a nucleic acid" means either an increase (stimulation) or a decrease (inhibition) in the level, activity, or expression of a miR-122a nucleic acid. As microRNAs negatively regulate protein-coding nucleic acids, inhibition of a microRNA generally results in stimulation of expression of one or more protein-coding nucleic acids regulated by the microRNA. Inhibition of miR-122a is a preferred form of modulation of a miR-122a nucleic acid. Stimulation is a preferred form of modulation of mRNAs regulated by miR-122a, such as ALDO A.

In one embodiment, the level, activity or expression of a miR-122a nucleic acid is inhibited to a degree that results in a phenotypic change, such as lowered serum cholesterol or reduced hepatic steatosis. "miR-122a nucleic acid level" or "miR-122a level" indicates the abundance of a miR-122a nucleic acid in a sample, such as an animal cell or tissue. "miR-122a level" may also indicate the relative abundance of a miR-122a nucleic acid in an experimental sample (e.g., tissue from an animal treated with an antisense compound targeted to miR-122a) as compared to a control sample (e.g., tissue from an untreated animal). "miR-122a activity" refers to the regulation of a protein-coding nucleic acid by miR-122a. "miR-122a expression" refers to the process by which mature miR-122a is derived from a DNA sequence that codes for miR-122a, which includes several steps, for example, transcription, Drosha processing, and Dicer processing. miR-122a expression may be regulated at a single step of this process, or at multiple steps.

As used herein, the term "small non-coding RNA" is used to encompass, without limitation, a polynucleotide molecule ranging from about 17 to about 450 nucleosides in length, which can be endogenously transcribed or produced exogenously (chemically or synthetically), but is not translated into a protein. As is known in the art, primary mRNAs (also known as pri-pre-miRNAs, pri-miRs and pri-miRNAs) range from around 70 nucleosides to about 450 nucleosides in length and often take the form of a hairpin structure. The primary mRNA is processed by Drosha to yield a pre-miRNA (also known as pre-mirs and foldback mRNA precursors), which ranges from around 50 nucleosides to around 110 nucleosides in length. The pre-miRNA is in turn processed by Dicer to yield a mRNA (also known as microRNAs, Mirs, miRs, miRs, and mature mRNAs), which ranges from 19 to 24 nucleosides in length. Small non-coding RNAs may include isolated single-, double-, or multiple-stranded molecules, any of which may include regions of intrastrand nucleobase complementarity, said regions capable of folding and forming a molecule with fully or partially double-stranded or multiple-stranded character based on regions of perfect or imperfect complementarity.

As used herein, a "miR-122a nucleic acid" includes pri-miR-122a, pre-miR-122a, and miR-122a. In the context of the present invention, pri-miR-122a is a primary mRNA, pre-miR-122a is a pre-miRNA, and miR-122a is a mature mRNA. "mature miR-122a" and "miR-122a" may be used interchangably herein.

As used herein, "miR-122a or a precursor thereof" encompasses miR-122a, pre-miR-122a, pri-miR-122a, or a primary RNA transcript from which miR-122a or its precursors are derived. As used herein, "miR-122a target nucleic acids" include pri-miR-122a, pre-miR-122a, and miR-122a.

In the context of the present invention, miR-122a (i.e. mature miR-122a) has the nucleobase sequence 5'-UGGAGUGUGACAAUGGUGUUUGU-3' (SEQ ID NO: 3). An alternative miR-122a, "miR-122a/b (Tuschl)", has been proposed in the art. miR-122a/b (Tuschl) lacks the 3'-most nucleoside relative to miR-122a and thus has the nucleobase sequence 5'-UGGAGUGUGACAAUGGUGUUUG-3' (SEQ ID NO: 4). One having ordinary skill in the art would understand that antisense compounds of the invention may target either miR-122a or miR-122a/b Tuschl.

As used herein, the term "miR-122a seed sequence" refers to nucleosides 2 through 8 from the 5'-end of the miR-122a sequence. In the context of the present invention, the miR-122a seed sequence is 5'-GGAGUGU-3'

The present invention also provides antisense compounds known as "ir-122a mimics", wherein the antisense compounds include one or more modifications or structural elements or motifs that render the compound capable of mimicking or replacing miR-122a or a precursor thereof.

Therapeutics

The specificity and sensitivity of antisense compounds targeting miR-122a, and compositions thereof, can be harnessed by those of skill in the art for therapeutic uses. Numerous clinical trials testing antisense compounds to other targets in a variety of therapeutic areas are presently underway.

A "human in need of treatment" or "subject in need of treatment" includes humans or subjects diagnosed as having or being susceptible to a disease or condition that can be treated, ameliorated, or prevented by the administration of an antisense compound targeted to a miR-122a nucleic acid. Such diseases or conditions include, but are not limited to, hypercholesterolemia, hypertriglyceridemia, hyperfattyacidemia, or hyperlipidemia, nonalcoholic fatty liver disease, hepatic steatosis (including non-alchoholic steatohepatitis and steatohepatitis), and metabolic syndrome. Subjects in need of treatment may include subjects diagnosed with HCV who also have one or more of the diseases or conditions mentioned herein, such as, for example, hypercholesterolemia or hepatic steatosis. Diagnosis of any of the aforementioned diseases or conditions routinely occurs in a clinical setting, for example, by a physician. Humans or subjects in need of treatment include those who are identified by a medical professional, such as a physician, to have risk factors for cardiovascular disease and/or risk determinants of metabolic syndrome.

As used herein, a "therapeutically effective amount" is an amount of an antisense compound targeted to a miR-122a nucleic acid that, when administered to a human having one or more of the aforementioned diseases or conditions, results in a clinically desirable outcome. Such clinically desirable outcomes may include, without limitation, lowered serum total cholesterol, lowered serum LDL-cholesterol, lowered serum triglycerides, lowered liver triglycerides, reduced steatosis, improved liver function, or increased fatty acid oxidation.

As used herein, a "prophylactically effective amount" is an amount of an antisense compound targeted to a miR-122a nucleic acid that, when administered to a human, prevents or reduces the susceptibility of the human to one or more of the aforementioned diseases or conditions. Prevention or reduction of the susceptibility of the human to the aforementioned diseases or conditions may be accomplished by preventing elevated serum total cholesterol, elevated serum LDL-cholesterol, elevated serum triglycerides, elevated liver triglycerides, hepatic steatosis, aberrant liver function, or reductions in fatty acid oxidation.

As used herein, the term "prevention" means to delay or forestall onset or development of a condition or disease for a period of time, preferably for weeks, months or years. As used herein, the term "amelioration" means a lessening of the severity of a condition or a disease, as evidenced by an improvement of one or more of the surrogate indicators disclosed herein. The improvement of such indicators may be determined by subjective or objective measures which are known to those skilled in the art. As used herein, "treatment" means to administer a composition of the invention to effect an alteration or improvement of the disease or condition. Prevention, amelioration, and/or treatment may require administration of multiple doses of an antisense compound targeted to a miR-122a nucleic acid to alter the course of the condition or disease. Moreover, a single antisense compound may be used in a single individual for the purposes of achieving any combination of prevention, amelioration, or treatment of a condition or disease, and such combinations may be pursued concurrently or sequentially. Antisense compounds of the present invention may, in some instances, be administered with other treatments.

A suitable method of administration is parenteral administration, which includes, for example, intravenous administration, subcutaneous administration, and intraperitoneal administration. The present invention provides the use of an antisense compound targeted to a miR-122a nucleic acid for the preparation of a medicament that is administered parenterally, for example, intravenously or subcutaneously.

As used herein, the term "serum marker of cardiovascular disease risk" includes risk factors recognized by medical professionals, including those set forth by the National Cholesterol Education Program (NCP), such as elevated serum cholesterol, elevated serum triglycerides, or elevated serum lipoprotein. Serum cholesterol further comprises serum total cholesterol and serum LDL-cholesterol. Serum lipoproteins further comprise serum ApoB-100 protein. In a clinical setting, serum markers of cardiovascular disease risk are measured to determine the need for treatment or prevention of a disease or condition described herein. The guidelines for lipid lowering therapy were established in 2001 by Adult Treatment Panel III (ATP III) of the NCEP, and updated in 2004 (Grundy et al., Circulation, 2004, 110, 227-239). The guidelines include determining LDL-cholesterol, total cholesterol, and HDL-cholesterol levels (i.e., determining lipoprotein levels). According to the most recently established guidelines, LDL-cholesterol levels of 130-159 mg/dL, 160-189 mg/dL, and greater than or equal to 190 mg/dL are considered borderline high, high, and very high, respectively. Total cholesterol levels of 200-239 and greater than or equal to 240 are considered borderline high and high, respectively. HDL-cholesterol levels of less than 40 are considered low. Serum triglyceride levels of 150-199, 200-499, and greater than or equal to 500 are considered borderline high, high, and very high, respectively. The serum cholesterol level (e.g. LDL-cholesterol, total cholesterol) and/or serum triglyceride level at which treatment is initiated depends upon the presence of clinical atherosclerotic disease that confers a high risk for coronary heart disease, such as clinical coronary heart disease, symptomatic carotid artery disease, peripheral arterial disease, and or abdominal aortic aneurysm, as well as additional risk factors, such as cigarette smoking, hypertension, low HDL-cholesterol, family history of coronary heart disease, and age. A subject' response to treatment is used by a physician to determine the amount and duration of treatment.

The NCEP ATP III has also established criteria for the diagnosis of metabolic syndrome when three or more of five risk determinants are present. "Metabolic syndrome" is defined as a clustering of lipid and non-lipid cardiovascular risk factors of metabolic origin. It is closely linked to the generalized metabolic disorder known as insulin resistance. The five risk determinants are abdominal obesity defined as waist circumference of greater than 102 cm for men or greater than 88 cm for women, triglyceride levels greater than or equal to 150 mg/dL, HDL cholesterol levels of less than 40 mg/dL for men and less than 50 mg/dL for women, blood pressure greater than or equal to 130/85 mm Hg and fasting glucose levels greater than or equal to 110 mg/dL. These determinants can be readily measured in clinical practice (*JAMA*, 2001, 285, 2486-2497).

One of skill in the art will readily appreciate that a physician may modify cardiovascular risk determination for individual patients, in cases where more or less aggressive therapy is needed. One of skill will also understand the scope of the invention includes the practice of the methods herein as applied to any altered guidelines provided by the NCEP, or other entities that establish guidelines for physician's used in treating any of the diseases or conditions listed here, for determining cardiovascular disease risk and diagnosing metabolic syndrome.

The embodiments herein provide the use of an antisense compound targeted to a miR-122a nucleic acid in the preparation of a medicament for lowering a serum indicator of cardiovascular disease risk, wherein the serum indicator is selected from elevated serum total cholesterol, elevated serum LDL-cholesterol, or elevated serum triglycerides.

The difficulty in directly measuring miR-122a levels, activity or expression following the administration of antisense compounds targeted to a miR-122a nucleic acid necessitates the use of surrogate indicators to assess the effects of administration of antisense compounds of the invention. Surrogate indicators are used to evaluate phenotypic changes that result from antisense inhibition of miR-122a. Surrogate indicators are often found in the serum, or alternatively in the plasma, of an animal. Methods of obtaining serum or plasma samples for analysis and methods of preparation of the serum samples to allow for analysis are well known to those skilled in the art. With regard to measurements of lipoproteins, cholesterol, and triglyceride, the terms "serum" and "plasma" are herein used interchangeably.

In the context of the present invention, "surrogate indicators" include serum indicators of cardiovascular disease risk, such as serum LDL-cholesterol levels, and serum total cholesterol levels, and serum triglyceride levels. Serum indicators further include serum transaminase levels. In the context of the present invention, "serum LDL-cholesterol levels" refer to the amounts of cholesterol that are carried in serum LDL particles, and are typically measured as mg/dL or nmol/L. "Serum total cholesterol levels", also expressed as mg/dL, refers to the sum of all different types of serum cholesterol, including, among others, LDL-cholesterol and HDL-cholesterol.

Preferred alterations in surrogate indicators of miR-122a inhibition include lowered serum LDL-cholesterol levels, lowered serum triglyceride levels, lowered lipoprotein levels. These aforementioned alterations are clinically desirable and are useful for the prevention, amelioration and/or treatment of the diseases and disorders disclosed herein.

"Serum lipoproteins" include without limitation apolipoprotein B (ApoB-100), low-density lipoprotein (LDL), and very low-density lipoprotein (VLDL).

Methods for the detection of hepatic steatosis are well known in the art, and include magnetic resonance imaging, computed tomography, and ultrasonagraphy. Methods used for the detection of hepatic steatosis may also be used to monitor the prevention, amelioration and/or treatment of the diseases and disorders disclosed herein.

In the context of the present invention, the term "improved hepatic function" or "improved liver function" refers to the improvement in the regular functions performed by the liver of an animal. One non-limiting example of a test for liver function involves the measurement of serum transaminases, which are additional surrogate indicators, wherein a reduction in serum transaminases such as alanine aminotransferase or aspartamine arinotransferase indicates an improvement in liver function. "Serum transaminase levels" refer to the abundance of transaminase in the serum (typically expressed as units/dL), and include "serum alanine aminotransferase levels" and "serum aspartamine aminotransferase levels." Increases in these enzymes are frequently associated with inflammation of the liver or liver cell death and, in some cases, can be caused by a condition such as hyperlipidemia, hypercholesterolemia, hypertriglyceridemia, or hyperlipidemia. Reductions in serum transaminases are clinically desirable and are useful for the prevention, amelioration and/or treatment of the diseases and disorders disclosed herein.

The term "nonalcoholic fatty liver disease" (NAFLD) encompasses a disease spectrum ranging from simple triglyceride accumulation in hepatocytes (hepatic steatosis) to hepatic steatosis with inflammation (steatohepatitis), fibrosis, and cirrhosis. Nonalcoholic steatohepatitis (NASH) occurs from progression of NAFLD beyond deposition of triglycerides. A second physiological insult capable of inducing necrosis, inflammation, and fibrosis is required for development of NASH. Candidates for the second insult can be grouped into broad categories: factors causing an increase in oxidative stress and factors promoting expression of proinflammatory cytokines. It has been suggested that increased liver triglycerides lead to increased oxidative stress in hepatocytes of animals and humans, indicating a potential cause-and-effect relationship between hepatic triglyceride accumulation, oxidative stress, and the progression of hepatic steatosis to NASH (Browning and Horton, J. Clin. Invest., 2004, 114, 147-152). Hypertriglyceridemia and hyperfatty-acidemia can cause triglyceride accumulation in peripheral tissues (Shimamura et al., Biochem. Biophys. Res. Commun., 2004, 322, 1080-1085). In the context of the present invention, additional clinically desirable outcomes include reductions in hepatic steatosis, steatohepatisis, fibrosis or cirrhosis.

Diseases or conditions described herein, such as elevated serum LDL-cholesterol or hepatic steatosis, may occur in humans diagnosed with HCV infection. Accordingly, the methods provided herein may also be used in subjects diagnosed with HCV infection. Additionally, the present invention provides the use of an antisense compound targeted to a miR-122a nucleic acid in the preparation of a medicament for lowering serum cholesterol, serum triglycerides or serum lipoproteins in an animal having HCV.

Drug Discovery

The antisense compounds and compositions of the present invention can additionally be utilized for research and drug discovery.

For use in research, antisense compounds of the present invention are used to interfere with the normal function of miR-122a target nucleic acids. Expression patterns within cells or tissues treated with one or more antisense compounds or compositions of the invention are compared to control cells or tissues not treated with the antisense compounds or compositions and the patterns produced are analyzed for differential levels of nucleic acid expression as they pertain, for example, to disease association, signaling pathway, cellular localization, expression level, size, structure or function of the genes examined. These analyses can be performed on stimulated or unstimulated cells and in the presence or absence of other compounds that affect expression patterns. By way of example, antisense compounds targeted to miR-122a were used to elucidate the metabolic pathways that are affected by miR-122a regulation.

For use in drug discovery, antisense compounds of the present invention are used to elucidate relationships that exist between miR-122a, or a precursor thereof and a disease state, phenotype, or condition. These methods include detecting or modulating a miR-122a nucleic acid comprising contacting a sample, tissue, cell, or organism with the antisense compounds and compositions of the present invention, measuring the levels of the target miR-122a nucleic acid and/or the levels of downstream gene products including mRNA or proteins encoded thereby, and further evaluating phenotypic changes at some time after treatment. These methods can also be performed in parallel or in combination with other experiments to determine the function of unknown genes for the process of target validation or to determine the validity of a particular miR-122a target nucleic acid as a target for treatment or prevention of a disease. By way of example, as described herein, antisense compounds targeted to miR-122a were used to effect phenotypic changes such as lowered serum cholesterol, lowered liver triglycerides, and reduced hepatic steatosis.

Antisense Compounds

In the context of the present invention, the term "oligomeric compound(s)" refers to polymeric structures which are capable of hybridizing to at least a region of an RNA molecule. Generally, an oligomeric compound is "antisense" to a target nucleic acid when, written in the 5' to 3' direction, it comprises the reverse complement of the corresponding region of the target nucleic acid. Such oligomeric compounds are known as "antisense compounds", which include, without limitation, oligonucleotides (i.e. antisense oligonucleotides), oligonucleosides, oligonucleotide analogs, oligonucleotide mimetics and combinations of these. In general, an antisense compound comprises a backbone of linked monomeric subunits (sugar moieties) where each linked monomeric subunit is directly or indirectly attached to a heterocyclic base moiety. Modifications to antisense compounds encompass substitutions or changes to internucleoside linkages, sugar moieties, or heterocyclic base moieties, such as those described below. As used herein, the term "modification" includes substitution and/or any change from a starting or natural nucleoside or nucleotide. Modified antisense compounds are often preferred over native forms because of desirable properties such as, for example, enhanced cellular uptake, enhanced affinity for nucleic acid target, increased stability in the presence of nucleases, or increased inhibitory activity. Antisense compounds are often defined in the art to comprise the further limitation of, once hybridized to a target, being able to induce or trigger a reduction in target gene expression or target gene activity. In one embodiment, the antisense compounds trigger a reduction in the levels, activity or expression of a miR-122a nucleic acid target.

Antisense compounds are routinely prepared linearly but can be joined or otherwise prepared to be circular and may also include branching. Separate antisense compounds can hybridize to form double stranded compounds that can be blunt-ended or may include overhangs on one or both termini.

The antisense compounds in accordance with this invention comprise from 15 to 30 nucleosides in length, i.e., from 15 to 30 linked nucleosides. One of skill in the art will appreciate that this embodies antisense compounds of 15, 16, 17, 18, 19, 20, 21, 22, 23, 24, 25, 26, 27, 28, 29, or 30 nucleosides in length. In one embodiment, the antisense compounds of the invention are 17 to 25 nucleosides in length, as exemplified herein.

In preferred embodiments, the antisense compounds of the invention are 19, 20, 21, 22 or 23 nucleosides in length.

As used herein, the term "about" means ±5% of the variable thereafter.

"Complementary," as used herein, refers to the capacity for hybridization between nucleobases. An antisense compound and the target nucleic acid are "fully complementary" to each other when each nucleobase of the antisense compound is complementary to an equal number of nuclebases in the target nucleic acid. For example, an antisense compound 23 nucleosides in length targeted to miR-122a is fully complementary to miR-122a when each of the 23 nucleobases in the antisense compound is complementary to miR-122a. The antisense compound and the target nucleic acid are "essentially fully complementary" to each other when the degree of precise base pairing permits stable and specific binding between the antisense compound and a target nucleic acid, so that the antisense compound inhibits the level, activity or expression of the target nucleic acid. Antisense compounds having one or two non-complementary nucleobases with respect to a miR-22a target nucleic acid are considered essentially fully complementary. "Sufficiently complementary" may be used in place of "essentially fully complementary".

In the context of this invention, "hybridization" means the pairing of nucleobases of an antisense compound with corresponding nucleobases in a target nucleic acid. In the context of the present invention, the mechanism of pairing involves hydrogen bonding, which may be Watson-Crick, Hoogsteen or reversed Hoogsteen hydrogen bonding, between corresponding nucleobases. For example, adenine and thymine are complementary nucleobases that pair through the formation of hydrogen bonds. Both natural and modified nucleobases are capable of participating in hydrogen bonding. Hybridization can occur under varying circumstances.

It is understood in the art that the sequence of the antisense compound need not be fully complementary to that of its target nucleic acid to be active in inhibiting the activity of the target nucleic acid. Moreover, an antisense compound may hybridize over one or more segments such that intervening or adjacent segments are not involved in the hybridization (e.g., a bulge, a loop structure or a hairpin structure). In some embodiments there are "non-complementary" positions, also known as "mismatches", between the antisense compound and the target nucleic acid, and such non-complementary positions may be tolerated between an antisense compound and the target nucleic acid provided that the antisense compound remains specifically hybridizable to the target nucleic acid. A "non-complementary nucleobase" means a nucleobase of an antisense compound that is unable to undergo precise base pairing with a nucleobase at a corresponding position in a target nucleic acid. As used herein, the terms "non-complementary" and "mismatch" are interchangable. Up to 3 non-complementary nucleobases are often tolerated in an antisense compound without causing a significant decrease in the ability of the antisense compound to modulate the activity, level or function of a target nucleic acid. In preferred embodiments, the antisense compound contains no more than 2, or no more than 1, non-complementary nucleobases with respect to a miR-122a target nucleic acid. For example, an antisense compound 23 nucleosides in length, 22 of which are able to undergo precise base pairing with nucleobases in corresponding positions in a target nucleic acid, and one of which is not able to undergo such base pairing, is considered to have one non-complementary nucleobase. The location of such a non-complementary nucleobase at the 5' end or 3' end of the antisense compound is preferred, however, the non-complementary nucleobase may be at any position in the antisense compound. In some embodiments, non-complementary nucleobases are preferred outside of the region of the antisense compound which is complementary to the seed sequence of miR-122a. When two or more non-complementary nucleobases are present, they may be contiguous (i.e. linked) or non-contiguous.

In other embodiments of the invention, the antisense compounds comprise at least 90% sequence complementarity to a miR-122a target nucleic acid. In further embodiments of the invention, the antisense compounds comprise at least 95% sequence complementarity to a miR-122a target nucleic acid. For example, an antisense compound in which 22 of 23 nucleobases of the antisense compound are complementary (i.e. one nucleobase is non-complementary) to a miR-122a nucleic acid would represent 95.6% complementarity. Likewise, an antisense compound in which 21 of the 23 nucleobases are complementary (i.e. two nucleobases are non-complementary) to a miR-122a nucleic acid would represent 91.3% complementarity. Percent complementarity of an antisense compound with a region of a target nucleic acid can be determined routinely by those having ordinary skill in the art, and may be accomplished using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

In the present invention the phrase "stringent hybridization conditions" or "stringent conditions" refers to conditions under which an antisense compound of the invention will hybridize to its target sequence, but to a minimal number of other sequences. Stringent conditions are sequence-dependent and will vary with different circumstances and in the context of this invention; "stringent conditions" under which antisense compounds hybridize to a target sequence are determined by the nature and composition of the antisense compounds and the assays in which they are being investigated. One having ordinary skill in the art will understand variability in the experimental protocols and be able to determine when conditions are optimal for stringent hybridization with minimal non-specific hybridization events.

Antisense compounds may have a defined percent identity to a SEQ ID NO, or an antisense compound having a specific ISIS number. This identity may be over the entire length of the antisense compound, or over less than the entire length of the antisense compound. It is understood by those skilled in the art that an antisense compound need not have an identical sequence to those described herein to function similarly to the antisense compounds described herein. Shortened or truncated versions of antisense compounds taught herein have one, two or more nucleosides deleted, and fall within the scope of the invention. When an antisense compound has two or more deleted nucleosides, the deleted nucleosides may be adjacent to each other, for example, in an antisense compound having two nucleosides truncated from the 5' end (5' truncation), or alternatively from the 3' end (3' truncation), of the antisense compound. Alternatively, the delelted nucleosides may be dispersed through out the antisense, for example, in an antisense compound having one nucleoside deleted from the 5' end and one nucleoside deleted from the 3' end.

Also falling within the scope of the invention are lengthened versions of antisense compounds taught herein, i.e. antisense compounds having one or more additional nucleosides relative to an antisense compound disclosed herein. When two are more additional nucleosides are present, the added nucleosides may be adjacent to each other, for example, in an antisense compound having two nucleosides added to the 5' end (5' addition), or alternatively to the 3' end (3' addition), of the antisense compound. Alternatively, the added nucleosides may be dispersed throughout the antisense compound, for example, in an antisense compound having one nucleoside added to the 5' end and one nucleoside added to the 3' end.

Percent identity of an antisense compound is calculated according to the number of nucleobases that are identical to the SEQ ID NO or antisense compound to which it is being compared. Such calculations are well within the ability of those skilled in the art. For example, a 21 nucleoside antisense compound having the same nucleobase sequence as nucleosides 2-21 of a 23 nucleoside antisense compound is 91.3% identical to the 23 nucleoside antisense compound. Alternatively, a 24 nucleoside antisense compound that differs in sequence only by the addition of one nucleoside relative to a 23 nucleoside antisense compound may have 100% identity over 23 nucleosides, but 95.8% identity overall.

"Targeting" an antisense compound to a particular nucleic acid molecule, including a miR-122a nucleic acid, in the context of this invention, can be a multistep process. The process usually begins with the identification of a target nucleic acid whose levels, expression or function is to be modulated. In the context of the present invention, the target nucleic acid is a miR-122a target nucleic acid.

The targeting process usually also includes determination of at least one target segment within a miR-122a target nucleic acid for the interaction to occur such that the desired effect, e.g., modulation of levels, activity, or expression, will result. As used herein, a "target segment" means a sequence of a miR-122a nucleic acid to which one or more antisense compounds are complementary. Multiple antisense compounds complementary to a given target segment may or may not have overlapping sequences. Within the context of the present invention, the term "target site" is defined as a sequence of a miR-122a nucleic acid to which one nucleobase sequence is complementary. For example, the nucleobase sequence of SEQ ID NO: 8 is complementary to target site 27 to 49 of SEQ ID NO: 5, and the nucleobase sequence of SEQ ID NO: 2 is complementary to target site 29 to 51 of SEQ NO: 5. Nucleosides 27 to 51 of SEQ ID NO: 5 thus represent a target segment of SEQ ID NO: 5. In some embodiments, a target segment and target site will be represented by the same nucleobase sequence.

Target sites and target segments may also be found in an mRNA gene from which a pri-miR-122a is derived, which may be found as a solitary transcript, or it may be found within a 5' untranslated region (5UTR), within in an intron, or within a 3' untranslated region (3UTR) of a gene.

Antisense compounds of the invention may be also be described as complementary to a portion of a target site. A "portion" is defined as at least 18 contiguous nucleosides of a target site. In other embodiments, a portion is 19 or 20 contiguous nucleosides of a target site. In preferred embodiments, a portion is 21 or 22 contiguous nucleosides of a target site.

Once one or more target segments or target sites have been identified, antisense compounds are designed to be sufficiently complementary to the target segments or target sites, i.e., hybridize sufficiently well and with sufficient specificity, to give the desired effect. The desired effect may include, but is not limited to modulation of the levels, expression or activity of the a miR-122a target nucleic acid. Desired effects further include phenotypic changes.

The antisense compounds of the invention may be in the form of single-stranded, double-stranded, circular or hairpin antisense compounds and may contain structural elements such as internal or terminal bulges or loops. Once introduced to a system, the antisense compounds of the invention may elicit or inhibit the action of one or more enzymes or proteins to effect modulation of the levels, expression or function of the target nucleic acid. One non-limiting example of such a protein is the Drosha RNase III enzyme. A further non-limiting example involves the enzymes of the RISC complex.

Antisense compounds or compositions of the invention may be used to induce potent and specific modulation of gene function through interactions with or mimicry of small non-coding RNAs that are processed by the RISC complex. These compounds include single-stranded antisense compounds that bind in a RISC complex, double-stranded antisense/sense pairs of antisense compounds, or single-stranded antisense compounds that include both an antisense portion and a sense portion.

Oligonucleotide Synthesis

Antisense compounds and phosphoramidites are made by methods well known to those skilled in the art. Oligomerization of modified and unmodified nucleosides is performed according to literature procedures for DNA like compounds (Protocols for Oligonucleotides and Analogs, Ed. Agrawal (1993), Humana Press) and/or RNA like compounds (Scaringe, Methods (2001), 23, 206-217. Gait et al., Applications of Chemically synthesized RNA in RNA:Protein Interactions, Ed. Smith (1998), 1-36. Gallo et al., Tetrahedron (2001), 57, 5707-5713) synthesis as appropriate. RNA oligomers can be synthesized by methods disclosed herein or purchased from various RNA synthesis companies such as for example Dharmacon Research Inc., (Lafayette, Colo.).

Irrespective of the particular protocol used, the antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

Methods of isolation and analysis of oligonucleotides are well known in the art. A 96-well plate format is particularly useful for the synthesis, isolation and analysis of oligonucleotides.

RNA Synthesis

Methods of RNA synthesis are well known in the art (Scaringe, S. A. Ph.D. Thesis, University of Colorado, 1996; Scaringe, S. A., et al., *J. Am. Chem. Soc.,* 1998, 120, 11820-11821; Matteucci, M. D. and Caruthers, M. H. *J. Am. Chem. Soc.,* 1981, 103, 3185-3191; Beaucage, S. L. and Caruthers, M. H. *Tetrahedron Lett.,* 1981, 22, 1859-1862; Dahl, B. J., et al., *Acta Chem. Scand,* 1990, 44, 639-641; Reddy, M. P., et al., *Tetrahedrom Lett.,* 1994, 25, 4311-4314; Wincott, F. et al., *Nucleic Acids Res.,* 1995, 23, 2677-2684; Griffin, B. E., et al., *Tetrahedron,* 1967, 23, 2301-2313; Griffin, B. E., et al., *Tetrahedron,* 1967, 23, 2315-2331).

Antisense Compound Modifications

Any of the antisense compounds taught herein may contain modifications which confer desirable pharmacokinetic and/or pharmacodynamic properties to the antisense compound including, but are not limited to, improved binding affinity, stability, charge, localization or uptake. Further, modified synthetic antisense compounds of the present invention may be designed to mimic endogenous small non-coding RNAs.

As is known in the art, a nucleoside is a base-sugar combination. The base (also known as nucleobase) portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. In addition, linear compounds may have internal base (i.e. nucleobase) complementarity and may therefore fold in a manner as to produce a fully or partially double-stranded structure. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In the context of this invention, the term "oligonucleotide" refers generally to an oligomer or polymer of ribonucleic acid (RNA) or deoxyribonucleic acid (DNA), and may be used to refer to unmodified oligonucleotides or oligonucleotide analogs. The term "unmodified oligonucleotide" refers generally to oligonucleotides composed of naturally occurring nucleobases, sugars, and covalent internucleoside linkages. The term "oligonucleotide analog" refers to oligonucleotides that have one or more non-naturally occurring nucleobases, sugars, and/or internucleoside linkages. Such non-naturally occurring oligonucleotides are often selected over naturally occurring forms because of desirable properties such as, for example, enhanced cellular uptake, enhanced affinity for other oligonucleotides or nucleic acid targets, increased stability in the presence of nucleases, or increased inhibitory activity.

Modified Internucleoside Linkages

Specific examples of antisense compounds useful in this invention include oligonucleotides containing modified, i.e. non-naturally occurring, internucleoside linkages. Such non-naturally internucleoside linkages are often selected over naturally occurring forms because of desirable properties such as, for example, enhanced cellular uptake, enhanced affinity for other oligonucleotides or nucleic acid targets and increased stability in the presence of nucleases.

Antisense compounds of the invention can have one or more modified internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be "oligonucleosides".

A suitable phosphorus-containing modified internucleoside linkage is the phosphorothioate internucleoside linkage. Additional modified internucleoside linkages containing a phosphorus atom therein include, for example, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleoside linkages is a 3' to 3', 5' to 5' or 2' to 2' linkage. Oligonucleotides having inverted polarity comprise a single 3' to 3' linkage at the 3'-most internucleoside linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126;

5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

In other embodiments of the invention, antisense compounds have one or more phosphorothioate and/or heteroatom internucleoside linkages, in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleoside linkage is represented as —O—P(=O)(OH)—O—$CH_2$—). The MMI type internucleoside linkages are disclosed in the above referenced U.S. Pat. No. 5,489,677. Amide internucleoside linkages are disclosed in the above referenced U.S. Pat. No. 5,602,240.

Modified internucleoside linkages that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Antisense compounds can also include an "oligonucleotide mimetic", which refers to oligonucleotides in which only the furanose ring or both the furanose ring and the internucleoside linkage are replaced with novel groups. Replacement of only the furanose ring is also referred to in the art as being a sugar surrogate. The heterocyclic base moiety or a modified heterocyclic base moiety is maintained for hybridization with an appropriate target nucleic acid. Oligonucleotide mimetics can include antisense compounds containing peptide nucleic acid (PNA) modifications. In PNA antisense compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA antisense compounds include, but are not limited to, U.S. Pat. Nos. 5,539,082; 5,714,331; and 5,719,262, each of which is herein incorporated by reference. Teaching of PNA antisense compounds can be found in Nielsen et al., *Science*, 1991, 254, 1497-1500. PNA has been modified to incorporate numerous modifications since the basic PNA structure was first prepared.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. Morpholino-based antisense compounds are disclosed in U.S. Pat. No. 5,034,506, issued Jul. 23, 1991. The morpholino class of antisense compounds have been prepared having a variety of different linking groups joining the monomeric subunits.

Another class of oligonucleotide mimetic is referred to as cyclohexenyl nucleic acids (CeNA).

The furanose ring normally present in an DNA/RNA molecule is replaced with a cyclohenyl ring. CeNA DMT protected phosphoramidite monomers have been prepared and used for antisense compound synthesis following classical phosphoramidite chemistry. Fully modified CeNA antisense compounds and oligonucleotides having specific positions modified with CeNA have been prepared and studied (see Wang et al., J. Am. Chem. Soc., 2000, 122, 8595-8602).

Modified Sugar Moieties

Antisense compounds of the invention may also contain one or more modified or substituted sugar moieties. The base moieties (natural, modified or a combination thereof) are maintained for hybridization with an appropriate nucleic acid target. Sugar modifications may impart nuclease stability, binding affinity or some other beneficial biological property to the antisense compounds. Representative modified sugars include carbocyclic or acyclic sugars, sugars having substituent groups at one or more of their 2', 3' or 4' positions, sugars having substituents in place of one or more hydrogen atoms of the sugar, and sugars having a linkage between any two other atoms in the sugar. Antisense compounds of particular use in the instant invention may comprise a sugar substituent group selected from: OH; halo; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are O(($CH_2$)$_n$O)$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON(($CH_2$)$_n$$CH_3$)$_2$, where n and m are from zero to about 10. Some oligonucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, S$CH_3$, OCN, F, Cl, Br, CN, $CF_3$, $OCF_3$, SO$CH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties.

One modification that imparts increased nuclease resistance and a very high binding affinity to nucleosides is the 2'-methoxyethoxy (2'-MOE or 2'—O$CH_2CH_2OCH_3$) side chain (Baker et al., J. Biol. Chem., 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'—O-methoxyethyl substituent also have been shown to be antisense inhibitors of gene expression with promising features for in vivo use (Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926). Relative to DNA, the oligonucleotides having the 2'-MOE modification displayed improved RNA affinity and higher nuclease resistance. Antisense compounds having one or more 2'-MOE modifications are capable of inhibiting mRNA activity in vitro and in vivo (Esau et al., J. Biol. Chem., 2004, 279, 52361-52365; U.S. Application Publication No. 2005/0261218).

Additional modifications include 2'-dimethylaminooxyethoxy, i.e., a O(CH$_2$)$_2$ON(CH$_3$)$_2$ group, also known as 2'-DMAOE, and 2'-dimethylaminoethoxyethoxy (also known in the art as 2'—O-dimethyl-amino-ethoxy-ethyl or 2'-DMAEOE), i.e., 2'-O—CH$_2$—O—CH$_2$—N(CH$_3$)$_2$.

Other sugar substituent groups include methoxy (—O—CH$_3$), aminopropoxy (—OCH$_2$CH$_2$CH$_2$NH$_2$), allyl (—CH$_2$—CH=CH$_2$), and —O-allyl (—O—CH$_2$—CH=CH$_2$). 2'-Sugar substituent groups may be in the arabino (up) position or ribo (down) position. Similar modifications may also be made at other positions on the antisense compound, particularly the 3' position of the sugar on the 3' terminal nucleoside or in 2'-5' linked oligonucleotides and the 5' position of 5' terminal nucleoside. Antisense compounds may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Representative substituents groups are disclosed in U.S. Pat. No. 6,172,209 entitled "Capped 2'-Oxyethoxy Oligonucleotides," hereby incorporated by reference in its entirety.

Representative cyclic substituent groups are disclosed in U.S. Pat. No. 6,271,358 entitled "RNA Targeted 2'-Oligomeric compounds that are Conformationally Preorganized," hereby incorporated by reference in its entirety.

Representative guanidino substituent groups are disclosed in U.S. Pat. No. 6,593,466 entitled "Functionalized Oligomers," hereby incorporated by reference in its entirety.

Representative acetamido substituent groups are disclosed in U.S. Pat. No. 6,147,200 which is hereby incorporated by reference in its entirety.

Representative dimethylaminoethyloxyethyl substituent groups are disclosed in International Patent Application PCT/US99/17895, entitled "2'—O-Dimethylaminoethyloxyethyl-Oligomeric compounds", filed Aug. 6, 1999, hereby incorporated by reference in its entirety.

An additional sugar modification includes a bicyclic sugar moiety, which has a 2', 4' bridge that forces the sugar ring into a locked 3'-endo conformational geometry. Bicyclic modifications imparts to an antisense compound greatly increased affinity for a nucleic acid target. Furthermore, nucleosides having bicyclic sugar modifications can act cooperatively with DNA and RNA in chimeric antisense compounds to enhance the affinity of a chimeric antisense compound for a nucleic acid target. Bicyclic sugar moieties can be represented by the formula 4'-(CH2)n-X-2', where X can be, for example, O or S. LNA™ is a bicyclic sugar moiety having a 4'—CH$_2$—O—2' bridge (i.e. X is O and n is 1). The alpha-L nucleoside has also been reported wherein the linkage is above the ring and the heterocyclic base is in the alpha rather than the beta-conformation (see U.S. Patent Application Publication No.: Application 2003/0087230). The xylo analog has also been prepared (see U.S. Patent Application Publication No.: 2003/0082807). Another bicyclic sugar moiety is ENA™, where in the aforementioned formula X is O and n is 2. The term 'locked nucleic acid' can also be used to describe any bicyclic sugar moiety that has a "locked" conformation.

Antisense compounds incorporating LNA™ and ENA™ analogs display very high duplex thermal stabilities with complementary DNA and RNA (Tm=+3 to +10 C), stability towards 3'-exonucleolytic degradation and good solubility properties.

The synthesis and preparation of the LNA™ monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Analogs of LNA™, such as phosphorothioate-LNA and 2'-thio-LNAs (i.e. 2'-S—CH2-4'), have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Some oligonucleotide mimetics have been prepared to include bicyclic and tricyclic nucleoside analogs (see Steffens et al., Helv. Chim. Acta, 1997, 80, 2426-2439; Steffens et al., J. Am. Chem. Soc., 1999, 121, 3249-3255; and Renneberg et al., J. Am. Chem. Soc., 2002, 124, 5993-6002). These modified nucleoside analogs have been oligomerized using the phosphoramidite approach and the resulting antisense compounds containing tricyclic nucleoside analogs have shown increased thermal stabilities (Tm's) when hybridized to DNA, RNA and itself. Antisense compounds containing bicyclic nucleoside analogs have shown thermal stabilities approaching that of DNA duplexes.

Another class of oligonucleotide mimetic is referred to as phosphonomonoester nucleic acid and incorporates a phosphorus group in the backbone. This class of olignucleotide mimetic is reported to have useful physical and biological and pharmacological properties in the areas of inhibiting gene expression.

Nucleobase Modifications

Antisense compounds of the invention may also contain one or more nucleobase (often referred to in the art simply as "base") modifications or substitutions which are structurally distinguishable from, yet functionally interchangeable with, naturally occurring or synthetic unmodified nucleobases. Such nucleobase modifications may impart nuclease stability, binding affinity or some other beneficial biological property to the antisense compounds. As used herein, "unmodified" or "natural" nucleobases include the purine bases adenine (A) and guanine (G), and the pyrimidine bases thymine (T), cytosine (C) and uracil (U). Modified nucleobases also referred to herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Some nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the antisense compounds of the invention. These include 5-substituted pyrimidines, 6-azapyrimidines and N-2, N-6 and O-6 substituted purines, including 2 aminopropyladenine, 5-propynyluracil and 5-propynylcytosine.

In one aspect of the present invention antisense compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines, and have been termed G-clamps or cytidine analogs.

Representative cytosine analogs that make 3 hydrogen bonds with a guanosine in a second strand include 1,3-diazaphenoxazine-2-one ($R_{10}$=O, $R_{11}$-$R_{14}$=H) (Kurchavov, et al., *Nucleosides and Nucleotides*, 1997, 16, 1837-1846), 1,3-diazaphenothiazine-2-one ($R_{10}$=S, $R_{11}$-$R_{14}$=H), (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one ($R_{10}$=O, $R_{11}$-$R_{14}$=F) (Wang, J.; Lin, K.-Y., Matteucci, M. Tetrahedron Lett. 1998, 39, 8385-8388). When incorporated into oligonucleotides, these base modifications were shown to hybridize with complementary guanine and the latter was also shown to hybridize with adenine and to enhance helical thermal stability by extended stacking interactions (also see U.S. Patent Application Publication 20030207804 and U.S. Patent Application Publication 20030175906, both of which are incorporated herein by reference in their entirety).

Tricyclic heterocyclic compounds and methods of using them that are amenable to the present invention are disclosed in U.S. Pat. No. 6,028,183, and U.S. Pat. No. 6,007,992, the contents of both are incorporated herein in their entirety.

The enhanced binding affinity of the phenoxazine derivatives together with their sequence specificity makes them valuable nucleobase analogs for the development of more potent antisense-based drugs. In fact, promising data have been derived from in vitro experiments demonstrating that heptanucleotides containing phenoxazine substitutions can activate RNaseH, enhance cellular uptake and exhibit an increased antisense activity (Lin, K-Y; Matteucci, M. J. Am. Chem. Soc. 1998, 120, 8531-8532). The activity enhancement was even more pronounced in case of G-clamp, as a single substitution was shown to significantly improve the in vitro potency of a 20 nucleoside 2'-deoxyphosphorothioate oligonucleotides (Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518).

Modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,750,692; 5,830,653; 5,763,588; 6,005,096; and 5,681,941, and U.S. Patent Application Publication 20030158403, each of which is incorporated herein by reference in its entirety.

Certain nucleobase substitutions, including 5-methylcytosinse substitutions, are particularly useful for increasing the binding affinity of the oligonucleotides of the invention. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'—O-methoxyethyl sugar modifications.

Conjugated Antisense Compounds

One substitution that can be appended to the antisense compounds of the invention involves the linkage of one or more moieties or conjugates which enhance the activity, cellular distribution or cellular uptake of the resulting antisense compounds. In one embodiment such modified antisense compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of the antisense compounds. Typical conjugate groups include cholesterol moieties and lipid moieties. Additional conjugate groups include carbohydrates, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that impart to the antisense compound properties such as improved uptake, enhanced resistance to degradation, and/or enhance hybridization with RNA. Groups that enhance the pharmacokinetic properties, in the context of this invention, include groups impart to the antisense compound properties such as improved uptake, distribution, metabolism or excretion. Representative conjugate groups are disclosed in International Patent Application PCT/US92/09196, filed Oct. 23, 1992 the entire disclosure of which is incorporated herein by reference.

Furthermore, the antisense compounds of the invention can have one or more conjugated moieties to facilitate the active or passive transport, localization, or compartmentalization of the antisense compound. Cellular localization includes, but is not limited to, localization to within the nucleus, the nucleolus, or the cytoplasm. Compartmentalization includes, but is not limited to, any directed movement of the antisense of the invention to a cellular compartment including the nucleus, nucleolus, mitochondrion, or imbedding into a cellular membrane. Furthermore, the antisense compounds of the invention comprise one or more conjugate moieties which facilitate posttranscriptional modification.

Antisense compounds used in the compositions of the present invention can also be modified to have one or more stabilizing groups that are generally attached to one or both termini of antisense compounds to enhance properties such as, for example, nuclease stability. Included in stabilizing groups are cap structures. By "cap structure" or "terminal cap moiety" is meant chemical modifications, which have been incorporated at either terminus of an antisense compound (see for example Wincott et al., WO 97/26270, incorporated by reference herein). These terminal modifications protect the antisense compounds having terminal nucleic acid molecules from exonuclease degradation, and can help in delivery and/or localization within a cell. The cap can be present at the 5'-terminus (5'-cap), or at the 3'-terminus (3'-cap), or can be present on both termini. For double-stranded antisense compounds, the cap may be present at either or both termini of either strand. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Antisense Compound Motifs

Antisense compounds of this invention may have the chemically modified subunits arranged in patterns enhance the inhibitory activity of the antisense compounds. These patterns are described herein as "motifs", and include uniformly modified, positionally modified, gapmer or gapped, alternating, hemimer, and blockmer.

As used in the present invention the term "uniform motif" is meant to include antisense compounds wherein each nucleoside bears the same type of sugar moiety, which may be a naturally occurring sugar or a modified sugar. Further, "uniformly modified motif," "uniform modifications," and "uniformly modified" are meant to include antisense compounds wherein each nucleoside bears the same type of sugar modification. Suitable sugar moieties include, but are not limited to 2'-O(CH$_2$)$_2$OCH$_3$ [2'-MOE], 2'—OCH$_3$ [2'—O-methyl], LNA and ENA™. For example, an antisense compound may be uniformly modified such that each sugar modification is a 2'-MOE sugar modification. Alternatively, an antisense compound may be uniformly modified such that each sugar modification is a 2'—O-methyl sugar modification.

As used in the present invention the term "gapped motif" or "gapmer" is meant to include an antisense compound having an internal region (also referred to as a "gap" or "gap segment") positioned between two external regions (also referred to as "wing" or "wing segment"). The regions are differentiated by the types of sugar moieties comprising each distinct region. The types of sugar moieties that are used to differentiate the regions of a gapmer include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include LNA™ or ENA™, among others). In general, each distinct region has a uniform motif sugar moieties within a region are uniform.

Gapped motifs or gapmers are further defined as being either "symmetric" or "asymmetric". A gapmer wherein the nucleosides of the first wing have the same sugar modifications as the nucleosides of the second wing is termed a symmetric gapped antisense compound. Symmetric gapmers can have, for example, an internal region comprising a first sugar moiety, and external regions each comprising a second sugar moiety, wherein at least one sugar moiety is a modified sugar moiety.

Gapmers as used in the present invention include wings that independently have from 1 to 7 nucleosides. The present invention therefore includes gapmers wherein each wing independently comprises 1, 2, 3, 4, 5, 6 or 7 nucleosides. The number of nucleosides in each wing can be the same or different. In one embodiment, the internal or gap region comprises from 17 to 21 nucleosides, which is understood to include 17, 18, 19, 20, or 21 nucleosides.

As used in the present invention the term "positionally modified motif" is meant to include a sequence of β-D-ribonucleosides, β-D-deoxyribonucleosides, or sugar-modified nucleosides wherein the sequence is interrupted by two or more regions comprising from 1 to about 8 sugar modified nucleosides wherein internal regions are generally from 1 to about 4 nucleosides. In other words, regions having a particular sugar moiety are separated by regions having different sugar moieties. Regions comprised of sugar modified nucleosides have the same sugar modification or vary such that one region has a different sugar modification than another region. Positionally modified motifs are not determined by the nucleobase sequence or the location or types of internucleoside linkages. The term positionally modified motif includes many different specific substitution patterns. A number of these substitution patterns have been prepared and tested in compositions.

The present invention includes antisense compounds having a positionally modified motif characterized by regions of 2'-sugar modified nucleosides which are separated by regions of a second, distinct 2'-sugar modified nucleosides or bicyclic modified sugar nucleosides. Preferred 2'-sugar moieties include 2'—O-methyl and 2'-MOE. Preferred bicyclic sugar moieties include LNA and ENA. The regions of 2'-sugar modified moieties may be 2 to 8 nucleosides in length, and the regions of bicyclic modified sugar moieties may be 1 or 2 nucleosides in length.

In one embodiment, antisense compounds of the invention are characterized by regions of two 2'-sugar modified nucleosides separated by regions of one bicyclic modified nucleoside, such that, beginning at the 5'-terminus, the antisense compounds have a 2'-sugar modified nucleoside at every first and second position, and a bicyclic modified nucleoside at every third position. Such a motif is described by the formula 5'-(A-A-B)$_n$(-A)nn-3', wherein A is a first sugar moiety, B is a second sugar moiety, n is 6 to 7 and nn is 0 to 2. In preferred embodiments, A is 2'-MOE and B is LNA. In further embodiments, A is 2'-O-methyl and B is LNA. In some embodiments, when such a motif would yield a bicyclic nucleoside at the 3'-terminus of the antisense compound (e.g, in an antisense compound 21 nucleosides in length), a 2'-sugar modified nucleoside is incorporated in place of a bicyclic modified nucleoside. For example, if n is 7, and nn is zero, a 2'-sugar modified nucleoside would be utilized at the 3'-terminal position in place of a bicyclic modified nucleoside.

Positionally modified motifs having less regular patterns are also included in the present invention. For example, the majority of the 2'-sugar modified regions may be 2 nucleosides in length, and a minority of 2'-sugar modified regions may be 1 nucleoside in length. Likewise, the majority of the bicyclic modified regions may be 1 nucleoside in length, and a minority of the bicyclic modified regions may be 2 nucleosides in length. One non-limiting example of such an antisense compound includes a positionally modified motif as described in the preceding paragraph, having one 2'-sugar modified region one nucleoside in length, and one bicyclic modified region two nucleosides in length.

As used in the present invention the term "alternating motif" is meant to include a contiguous sequence of two distinct alternating nucleosides for essentially the entire length of the compound. The pattern of alternation can be described by the formula: 5'-A(B-A)$_n$(-B)nn-3' where A and B are nucleosides differentiated by having at least different sugar moieties, nn is 0 or 1 and n is from about 7 to about 11. This permits antisense compounds from 17 to 24 nucleosides in length. This length range is not meant to be limiting as longer and shorter antisense compounds are also amenable to the present invention. This formula also allows for even and odd lengths for alternating antisense compounds wherein the 5'- and 3'-terminal nucleosides comprise the same (odd) or different (even) sugar moieties.

The "A" and "B" nucleosides comprising alternating antisense compounds of the present invention are differentiated from each other by having at least different sugar moieties. Each of the A and B nucleosides has a modified sugar moiety selected from β-D-ribonucleosides, β-D-deoxyribonucleosides, 2'-modified nucleosides (such 2'-modified nucleosides may include 2'-MOE, and 2'—O—CH3, among others), and bicyclic sugar modified nucleosides (such bicyclic sugar modified nucleosides may include LNA or ENA, among others). The alternating motif is independent from the nucleobase sequence and the internucleoside linkages. The internucleoside linkage can vary at each position or at particular selected positions or can be uniform or alternating throughout the antisense compound.

As used in the present invention the term "hemimer motif" is meant to include a sequence of nucleosides that have uniform sugar moieties (identical sugars, modified or unmodified) and wherein one of the 5'-end or the 3'-end has a sequence of from 2 to 12 nucleosides that are sugar modified nucleosides that are different from the other nucleosides in the hemimer modified antisense compound. An example of a typical hemimer is an antisense compound comprising a sequence of β-D-ribonucleosides or β-D-deoxyribonucleosides at one terminus and a sequence of sugar modified nucleosides at the other terminus. One hemimer motif includes a sequence of β-D-ribonucleosides or β-D-deoxyribonucleosides at one terminus, followed or preceded by a sequence of 2 to 12 sugar modified nucleosides at the other terminus. Another hemimer motif includes a sequence of β-D-ribonucleosides or β-D-deoxyribonucleosides at one terminus, followed or preceded by a sequence of 2 to 6 sugar modified nucleosides located at the other terminus, with from 2 to 4 sugar modified nucleosides being suitable as well. In a preferred embodiment of the invention, the hemimer antisense compound comprises a region of 2'-MOE modified nuculeosides and a region of β-D-deoxyribonucleosides. In one embodiment, the β-D-deoxyribonucleosides comprise less than 13 contiguous nucleosides within the antisense compound.

As used in the present invention the term "blockmer motif" is meant to include a sequence of nucleosides that have uniform sugars (identical sugars, modified or unmodified) that is internally interrupted by a block of sugar modified nucleosides that are uniformly modified and wherein the modification is different from the other nucleosides. More generally, antisense compounds having a blockmer motif comprise a sequence of β-D-ribonucleosides or β-D-deoxyribonucleosides having one internal block of from 2 to 6, or from 2 to 4 sugar modified nucleosides. The internal block region can be at any position within the antisense compound as long as it is not at one of the termini which would then make it a hemimer. The base sequence and internucleoside linkages can vary at any position within a blockmer motif.

Antisense compounds having motifs selected from uniform positionally modified, alternating, gapped, hemimer or blockmer may further comprise internucleoside linkage modifications or nucleobase modifications, such as those described herein.

"Chimeric antisense compounds" or "chimeras," in the context of this invention, are antisense compounds that at least 2 chemically distinct regions, each made up of at least one monomer unit, i.e., a nucleotide or nucleoside in the case of a nucleic acid based antisense compound. Accordingly, antisense compounds having a motif selected from positionally modified, gapmer, alternating, hemimer, or blockmer are considered chimeric antisense compounds.

Chimeric antisense compounds typically contain at least one region modified so as to confer increased resistance to nuclease degradation, increased cellular uptake, increased binding affinity for the target nucleic acid, and/or increased inhibitory activity. By way of example, an antisense compound may be designed to comprise a region that serves as a substrate for the cellular endonuclease RNase H, which cleaves the RNA strand of an RNA:DNA duplex. Activation of RNase H by an antisense compound having a cleavage region, therefore, results in cleavage of the RNA target, thereby enhancing the efficiency of the antisense compound. Alternatively, an antisense compound may be designed to comprise a region that imparts to the antisense compound increased affinity or activity such that antisense inhibition is achieved through a mechanism such as steric occlusion, rather than enzymatic cleavage.

Chemically modified nucleosides may also be employed to increase the binding affinity of a shortened or truncated antisense compound for its target nucleic acid. Consequently, comparable results can often be obtained with shorter antisense compounds that have such chemically modified nucleosides.

Any of the antisense compounds described herein, having motifs selected from uniform, positionally modified, alternating, gapmer, hemimer, or blockmer, may further comprise internucleoside linkage modifications and/or nucleobase modifications, such as those described herein.

Nucleosides, both native and modified, have a certain conformational geometry which affects their hybridization and affinity properties. The terms used to describe the conformational geometry of homoduplex nucleic acids are "A Form" for RNA and "B Form" for DNA. In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker.

This is consistent with Berger, et. al., Nucleic Acids Research, 1998, 26, 2473-2480, who pointed out that in considering the fliranose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., Nucleic Acids Res., 1993, 21, 2051-

2056). The structure of a hybrid duplex is intermediate between A- and B-form geometries, which may result in poor stacking interactions (Lane et al., Eur. J. Biochem., 1993, 215, 297-306; Fedoroff et al., J. Mol. Biol., 1993, 233, 509-523; Gonzalez et al., Biochemistry, 1995, 34, 4969-4982; Horton et al., J. Mol. Biol., 1996, 264, 521-533). The stability of the duplex formed between a target RNA and a synthetic sequence is central to therapies such as, but not limited to, antisense mechanisms, including RNase H-mediated and RNA interference mechanisms, as these mechanisms involved the hybridization of a synthetic sequence strand to an RNA target strand or steric hindrance.

One routinely used method of modifying the sugar puckering is the substitution of the sugar at the 2'-position with a substituent group that influences the sugar geometry. The influence on ring conformation is dependent on the nature of the substituent at the 2'-position. A number of different substituents have been studied to determine their sugar puckering effect.

In some embodiments of this invention, duplex stability can be enhanced by incorporating modified sugar moieties which exhibit A-form geometry. One of skill in the art can determine whether a given substituted sugar will have A-form geometry.

In one aspect of the present invention antisense compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA-like nucleosides so that particular properties of an antisense compound can be enhanced while maintaining the desirable 3'-endo conformational geometry. There is an apparent preference for an RNA type duplex (A form helix, predominantly 3'-endo) as a requirement (e.g. trigger) of RNA interference. Properties that are enhanced by using more stable 3'-endo nucleosides include, but are not limited to, modulation of one or more of the following: protein binding; protein off-rate; absorption and clearance; modulation of nuclease stability as well as chemical stability; modulation of the binding affinity and specificity of the antisense compound (affinity and specificity for enzymes as well as for complementary sequences); increased efficacy of RNA cleavage; and increase steric occulsion. The present invention provides antisense compounds designed to act as triggers of RNAi having one or more nucleosides modified in such a way as to favor a C3'-endo type conformation.

The conformation of modified nucleosides and the antisense compounds containing them can be estimated by various methods such as molecular dynamics calculations, nuclear magnetic resonance spectroscopy and CD measurements. Hence, modifications predicted to induce RNA-like conformations (A-form duplex geometry in an antisense compound context), are useful in the antisense compounds of the present invention. The synthesis of modified nucleosides amenable to the present invention are known in the art (see for example, Chemistry of Nucleosides and Nucleotides Vol 1-3, ed. Leroy B. Townsend, 1988, Plenum Press.)

In one aspect, the present invention is directed to antisense compounds that are designed to have enhanced properties compared to native RNA. One method to design optimized or enhanced antisense compounds involves each nucleoside of the selected sequence being scrutinized for possible enhancing modifications. One modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligonucleotide. The sequence can be further divided into regions and the nucleosides of each region evaluated for enhancing modifications that can be the result of a chimeric configuration. Consideration is also given to the 5' and 3'-termini as there are often advantageous modifications that can be made to one or more of the terminal nucleosides. The antisense compounds of the present invention may include at least one 5'-modified phosphate group on a single strand or on at least one 5'-position of a double-stranded sequence or sequences. Other modifications considered are internucleoside linkages, conjugate groups, substitute sugars or bases, substitution of one or more nucleosides with nucleoside mimetics and any other modification that can enhance the desired property of the antisense compound.

Unless otherwise defined herein, alkyl means $C_1$-$C_{12}$, $C_1$-$C_8$, or $C_1$-$C_6$, straight or (where possible) branched chain aliphatic hydrocarbyl.

Unless otherwise defined herein, heteroalkyl means $C_1$-$C_{12}$, $C_1$-$C_8$, or $C_1$-$C_6$, straight or (where possible) branched chain aliphatic hydrocarbyl containing at least one, or about 1 to about 3 hetero atoms in the chain, including the terminal portion of the chain. Suitable heteroatoms include N, O and S.

Unless otherwise defined herein, cycloalkyl means $C_3$-$C_{12}$, $C_3$-$C_8$, or $C_3$-$C_6$, aliphatic hydrocarbyl ring.

Unless otherwise defined herein, alkenyl means $C_2$-$C_{12}$, $C_2$-$C_8$, or $C_2$-$C_6$ alkenyl, which may be straight or (where possible) branched hydrocarbyl moiety, which contains at least one carbon-carbon double bond.

Unless otherwise defined herein, alkynyl means $C_2$-$C_{12}$, $C_2$-$C_8$, or $C_2$-$C_6$ alkynyl, which may be straight or (where possible) branched hydrocarbyl moiety, which contains at least one carbon-carbon triple bond.

Unless otherwise defined herein, heterocycloalkyl means a ring moiety containing at least three ring members, at least one of which is carbon, and of which 1, 2 or three ring members are other than carbon. The number of carbon atoms can vary from 1 to about 12, from 1 to about 6, and the total number of ring members varies from three to about 15, or from about 3 to about 8. Suitable ring heteroatoms are N, O and S. Suitable heterocycloalkyl groups include, but are not limited to, morpholino, thiomorpholino, piperidinyl, piperazinyl, homopiperidinyl, homopiperazinyl, homomorpholino, homothiomorpholino, pyrrolodinyl, tetrahydrooxazolyl, tetrahydroimidazolyl, tetrahydrothiazolyl, tetrahydroisoxazolyl, tetrahydropyrrazolyl, furanyl, pyranyl, and tetrahydroisothiazolyl.

Unless otherwise defined herein, aryl means any hydrocarbon ring structure containing at least one aryl ring. Suitable aryl rings have about 6 to about 20 ring carbons. Especially suitable aryl rings include phenyl, napthyl, anthracenyl, and phenanthrenyl.

Unless otherwise defined herein, hetaryl means a ring moiety containing at least one fully unsaturated ring, the ring consisting of carbon and non-carbon atoms. The ring system can contain about 1 to about 4 rings. The number of carbon atoms can vary from 1 to about 12, from 1 to about 6, and the total number of ring members varies from three to about 15, or from about 3 to about 8. Suitable ring heteroatoms are N, O and S. Suitable hetaryl moieties include, but are not limited to, pyrazolyl, thiophenyl, pyridyl, imidazolyl, tetrazolyl, pyridyl, pyrimidinyl, purinyl, quinazolinyl, quinoxalinyl, benzimidazolyl, benzothiophenyl, etc.

Unless otherwise defined herein, where a moiety is defined as a compound moiety, such as hetarylalkyl (hetaryl and alkyl), aralkyl (aryl and alkyl), etc., each of the sub-moieties is as defined herein.

Unless otherwise defined herein, an electron withdrawing group is a group, such as the cyano or isocyanato group that draws electronic charge away from the carbon to which it is attached. Other electron withdrawing groups of note include those whose electronegativities exceed that of carbon, for example halogen, nitro, or phenyl substituted in the ortho- or para-position with one or more cyano, isothiocyanato, nitro or halo groups.

Unless otherwise defined herein, the terms halogen and halo have their ordinary meanings. Suitable halo (halogen) substituents are F, Cl, Br, and I.

The aforementioned optional substituents are, unless otherwise herein defined, suitable substituents depending upon desired properties. Included are halogens (F, Cl, Br, I), alkyl, alkenyl, and alkynyl moieties, $NO_2$, $NH_3$ (substituted and unsubstituted), acid moieties (e.g. —$CO_2H$, —$OSO_3H_2$, etc.), heterocycloalkyl moieties, hetaryl moieties, aryl moieties, etc.

Phosphate protecting groups include those described in U.S. Pat. No. 5,760,209, U.S. Pat. No. 5,614,621, U.S. Pat. No. 6,051,699, U.S. Pat. No. 6,020,475, U.S. Pat. No. 6,326,478, U.S. Pat. No. 6,169,177, U.S. Pat. No. 6,121,437, U.S. Pat. No. 6,465,628 each of which is expressly incorporated herein by reference in its entirety.

Screening Antisense Compounds

Screening methods for the identification of effective modulators of miR-122a target nucleic acids are also comprehended by the instant invention and comprise the steps of contacting a miR-122a target nucleic acid, or portion thereof, with one or more candidate modulators, and selecting for one or more candidate modulators which inhibit the levels, expression or function of a miR-122a target nucleic acid. As described herein, the candidate modulator can be an antisense compound targeted to a pri-miRNA, or any portion thereof, including the mature mRNA, the Drosha recognition region, the Drosha cleavage region, the stem of the hairpin, or the loop of the hairpin. Candidate modulators further include small molecule compounds that bind to structured regions of miR-122a target nucleic acids, such as structured regions within pri-miR-122a. Once it is shown that the candidate modulator or modulators are capable of modulating, preferably decreasing, the levels, expression or function of a miR-122a target nucleic acid, the modulator may then be employed in further investigative studies, or for use as a target validation, research, diagnostic, or therapeutic agent in accordance with the present invention.

Compositions and Methods for Formulating Pharmaceutical Compositions

The present invention also include pharmaceutical compositions and formulations that include the antisense compounds and compositions of the invention. Compositions and methods for the formulation of pharmaceutical compositions are dependent upon a number of criteria, including, but not limited to, route of administration, extent of disease, or dose to be administered. Such considerations are well understood by those skilled in the art.

The antisense compounds and compositions of the invention can be utilized in pharmaceutical compositions by adding an effective amount of the compound or composition to a suitable pharmaceutically acceptable diluent or carrier. Use of the antisense compounds and methods of the invention may also be useful prophylactically.

The antisense compounds and compositions of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the antisense compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. This can include the incorporation of additional nucleosides at one or both ends of an antisense compound which are cleaved by endogenous nucleases within the body, to form the active antisense compound.

The term "pharmaceutically acceptable salts" refers to physiologically and pharmaceutically acceptable salts of the antisense compounds and compositions of the invention: i.e., salts that retain the desired biological activity of the parent compound and do not impart undesired toxicological effects thereto. Suitable examples include, but are not limited to, sodium and potassium salts.

In some embodiments, an antisense compound can be administered to a subject via an oral route of administration. The subject may be a mammal, such as a mouse, a rat, a dog, a guinea pig, a non-human primate, or a human. In certain embodiments, the subject may be in need of modulation of the level or expression a miR-122a nucleic acid, or in need of modulation of surrogate indicators as described here. In some embodiments, compositions for administration to a subject will comprise modified oligonucleotides having one or more modifications, as described herein.

Cell Culture and Antisense Compound Treatment

The effects of antisense compounds the level, activity or expression of miR-122a target nucleic acids, protein-coding RNAs regulated by miR-122a, can be tested in vitro in a variety of cell types. Cell types used for such analyses are available from commerical vendors (e.g. American Type Culture Collection, Manassus, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to: T-24 cells, A549 cells, normal human mammary epithelial cells (HMECs), MCF7 cells, T47D cells, BJ cells, B16-F10 cells, human vascular endothelial cells (HUVECs), human neonatal dermal fibroblast (NHDF) cells, human embryonic keratinocytes (HEK), 293T cells, HepG2, human preadipocytes, human differentiated adipocytes (preapidocytes differentiated according to methods known in the art), NT2 cells (also known as NTERA-2 cl.D1), and HeLa cells.

Treatment of Cells with Antisense Compounds

In general, when cells reach approximately 60-80% confluency, they are treated with antisense compounds of the invention.

One reagent commonly used to introduce antisense compounds into cultured cells includes the cationic lipid transfection reagent LIPOFECTIN® (Invitrogen, Carlsbad, Calif.). Antisense compounds are mixed with LIPOFECTIN® in OPTI-MEM® 1 (Invitrogen, Carlsbad, Calif.) to achieve the desired final concentration of antisense compound and a LIPOFECTIN® concentration that typically ranges 2 to 12 μg/mL per 100 nM antisense compound.

Another reagent used to introduce antisense compounds into cultured cells includes LIPOFECTAMINE® (Invitrogen, Carlsbad, Calif.). Antisense compound is mixed with LIPOFECTAMINE® in OPTI-MEM® 1 reduced serum medium (Invitrogen, Carlsbad, Calif.) to achieve the desired concentration of antisense compound and a LIPOFECTAMINE® concentration that typically ranges 2 to 12 µg/mL per 100 nM antisense compound.

Cells are treated with antisense compounds by routine methods well known to those skilled in the art. Cells are typically harvested 16-24 hours after antisense compound treatment, at which time RNA or protein levels of target nucleic acids are measured by methods known in the art and described herein. When the target nucleic acid is a mRNA, the RNA or protein level of a protein-coding RNA regulated by a mRNA may be measured to evaluate the effects of antisense compounds targeted to a mRNA. In general, when treatments are performed in multiple replicates, the data are presented as the average of the replicate treatments.

The concentration of antisense used varies from cell line to cell line. Methods to determine the optimal antisense concentration for a particular cell line are well known in the art. Antisense compounds are typically used at concentrations ranging from 1 nM to 300 nM.

RNA Isolation

RNA analysis can be performed on total cellular RNA or poly(A)+ mRNA. Methods of RNA isolation are well known in the art. RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of a mniR-122a nucleic acid, or modulation of a protein-coding RNA target of miR-122a (e.g. ALDO A), can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Additional examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression)(Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904), and mass spectrometry methods (To, Comb. Chem. High Throughput Screen, 2000, 3, 235-41).

Quantitative Real-Time PCR Analysis of Target RNA Levels

Quantitation of target RNA levels is accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well.

RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as GAPDH, or by quantifying total RNA using RIBOGREEN® (Molecular Probes, Inc. Eugene, Oreg.). GAPDH expression is quantified by real time PCR, by being run simultaneously with the target, multiplexing, or separately. Total RNA is quantified using RIBOGREEN® RNA quantification reagent (Molecular Probes, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to the target sequence, which includes a protein-coding RNA that is regulated by a miR-122a, such as ALDO A. Methods for designing real-time PCR probes and primers are well known in the art, and may include the use of software such as PRIMER EXPRESS® Software (Applied Biosystems, Foster City, Calif.).

Northern Blot Analysis of Target RNA Levels

Northern blot analysis is performed according to routine procedures known in the art. Higher percentage acrylamide gels, for example, 10 to 15% acrylamide urea gels, are generally used to resolve mRNA. Fifteen to twenty micrograms of total RNA is fractionated by electrophoresis through 10% acrylamide urea gels using a TBE buffer system (Invitrogen). RNA is transferred from the gel to HYBOND™-N+ nylon membranes (Amersham Pharmacia Biotech, Piscataway, N.J.) by electroblotting in an Xcell SURELOCK™ Minicell (Invitrogen, Carlsbad, Calif.). Membranes are fixed by UV cross-linking using a STRATALINKER® V Crosslinker 2400 (Stratagene, Inc, La Jolla, Calif.) and then probed using RAPID HYB™ buffer solution (Amersham) using manufacturer's recommendations for oligonucleotide probes.

A target specific DNA oligonucleotide probe with the sequence is used to detect the RNA of interest. Probes used to detect mRNAs are synthesized by commercial vendors such as IDT (Coralville, Iowa). The probe is 5' end-labeled with T4 polynucleotide kinase with (gamma-$^{32}$P) ATP (Promega, Madison, Wis.). To normalize for variations in loading and transfer efficiency membranes are stripped and re-probed for an RNA whose level is constant, such as GAPDH. For higher percentage acrylamide gels used to resolve mRNA, U6 RNA is used to normalize for variations in loading and transfer efficiency. U6 RNA. Hybridized membranes are visualized and quantitated using a STORM® 860 PHOSPHORIMAGER® System and IMAGEQUANT® Software V3.3 (Molecular Dynamics, Sunnyvale, Calif.).

Analysis of Protein Levels

Protein levels of a downstream target modulated or regulated by miR-122a, such as ALDO A, can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

In Vivo Studies

In accordance with the present invention, antisense compounds of the invention are tested in various animal models of disease, including normal, lean mice, ob/ob mice, db/db mice, and diet-induced obese mice, and mouse and rat models of diet induced obesity.

Leptin is a hormone produced by fat cells that regulates appetite. Deficiencies in this hormone in both humans and non-human animals leads to obesity. ob/ob mice have a mutation in the leptin gene which results in obesity and hyperglycemia. As such, these mice are a useful model for the investigation of obesity and diabetes and treatments designed to treat these conditions. ob/ob mice have higher circulating levels of insulin and are less hyperglycemic than db/db mice, which harbor a mutation in the leptin receptor. db/db mice have a mutation in the leptin receptor gene which results in obesity and hyperglycemia. As such, these mice are a useful model for the investigation of obesity and diabetes and treatments designed to treat these conditions. db/db mice, which have lower circulating levels of insulin and are more hyperglycemic than ob/ob mice which harbor a mutation in the leptin gene, are often used as a rodent model of type 2 diabetes.

C57Bl/6 mice are maintained on a standard rodent diet for use as control (lean) animals. Additionally, the C57BL/6 mouse strain is reported to be susceptible to hyperlipidemia-induced atherosclerotic plaque formation. Consequently, when these mice are fed a high-fat diet, they develop diet-induced obesity. Accordingly these mice are a useful model for the investigation of obesity and treatments designed to treat these conditions.

The Levin Model is a polygenic model of rats selectively bred to develop diet-induced obesity (DIO) associated with impaired glucose tolerance, dyslipidemia and insulin resistance when fed a high-fat diet (Levin, et al., *Am. J. Physiol*, 1997, 273, R725-30). This model is useful in investigating the antisense compounds of the present invention for their ability to affect obesity and related complications, such as impaired glucose tolerance, dyslipidemia and insulin resistance.

In order that the invention disclosed herein may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, GENBANK® accession numbers, and the like) cited in the present application is incorporated herein by reference in its entirety.

EXAMPLES

Example 1

Pri-mRNA Sequences

The sequence of pri-miR-122a was used in certain embodiments of the invention, for example, in the design of antisense compounds targeting a miR-122a nucleic acid. The sequence of the human pri-miR-122a was extracted from the sequence having GENBANK® accession number NT_033907.3 is incorpated herein as SEQ ID NO: 5 (UGGCUACAGAGU-UUCCUUAGCAGAGCUGUGGAGUGUGACAAUGG UGUUUGUGUCUAAAC UAUCAAACGCCAUUAUCA-CACUAAAUAGCUACUGCUAGGCAAUCCUUCCCU). The sequence of the mouse pri-miR-122a is incorporated herein as SEQ ID NO: 6 (UUCCUUAGCAGAGCUGUG-GAGUGUGACAAUGGUGUUUGUGUCCA-AACCAUCAAACGCCA UUAUCACACUAAAUAGC-UACUG). The sequence of the rat pri-miR-122a is incorporated herein as SEQ ID NO: 7 (UCCUUAGCA-GAGCUCUGGAGUGUGACAAUGGUGUUU-GUGUCCAAAACAUCAAACGCCAU CAUCACAC-UAAACAGCUACUG). The sequences are written in the 5' to 3' direction and are represented in the DNA form. It is understood that a person having ordinary skill in the art would be able to convert the sequence of the targets to their RNA form by simply replacing the thymidine (T) with uracil (U) in the sequence.

Example 2

Mature mRNA Sequences

Mature mRNAs found within the pri-miR-122a sequence were used in certain embodiments of the present invention, for example, in the design of antisense compounds targeting a miR-122a nucleic acid. Antisense compounds can also be designed to mimic miR-122a while incorporating certain chemical modifications that alter one or more properties of the mimic, thereby creating a construct with superior properties over the endogenous mRNA.

Mature miR-122a sequences are shown in Table 1. Mature miR-122a sequences from pri-miR-122a precursors have been proposed by several groups; consequently, two mature miR-22a sequences are disclosed in Table 1. The sequences are written in the 5' to 3' direction and are represented in the RNA form. It is understood that a person having ordinary skill in the art would be able to convert the sequence of the targets to a DNA form by simply replacing the uracil (U) with thymidine (T) in the sequence.

TABLE 1

Mature miR-122a found within pri-miR-122a

| Species | Name | miRNA sequence | SEQ ID NO |
|---------|------|----------------|-----------|
| Human | miR-122a | UGGAGUGUGACAAUGGUGUUUGU | 3 |
| Human | miR-122a, b (Tuschl) | UGGAGUGUGACAAUGGUGUUUG | 4 |
| Mouse | miR-124a_Ruvkun | UGGAGUGUGACAAUGGUGUUUGU | 3 |

TABLE 1-continued

Mature miR-122a found within pri-miR-122a

| Species | Name | miRNA sequence | SEQ ID NO |
|---------|------|----------------|-----------|
| Mouse | miR-172 (RFAM- M. mu.) | UGGAGUGUGACAAUGGUGUUUG | 4 |
| Rat | miR-122a | UGGAGUGUGACAAUGGUGUUUGU | 3 |
| Rat | miR-122a, b (Tuschl) | UGGAGUGUGACAAUGGUGUUUG | 4 |

Example 3

Antisense Compounds Targeting miR-122a

In accordance with the present invention, a series of antisense compounds was designed and synthesized to target various sites within miR-122a nucleic acids. The antisense compounds are analyzed for their effect on mRNA, pre-mRNA or pri-mRNA levels by Northern blotting or quantitative real-time PCR as described, supra, or they can be used in other assays to investigate the role of miR-122a or miR-122a downstream targets.

The target sites to which the following antisense compounds are complementary include mature miR-122a, as well as target sites of pri-miR-122a. For example, an antisense compound having the sequence of SEQ ID NO: 12 was designed to target the stem loop of the pri-miR-122a structure.

The nucleobase sequences and target sites of the antisense compounds of the invention are shown in Table 2. In Table 2, the target site is the sequence of SEQ ID NO: 5 to which the antisense compound is complementary. While the nucleobase sequences in Table 2 are shown having the DNA nucleobases "T", one of skill in the art understand that in RNA sequences, "T" is replaced with "U". For example, in the nucleobase sequence of the uniform RNA antisense compound ISIS 342970, "T" is replaced with "U".

TABLE 2

Sequences of antisense compounds targeting pri-miR-122a or miR-122a

| Sequence (5' to 3') | SEQ ID NO | Target site on SEQ ID NO: 5 |
|---------------------|-----------|------------------------------|
| AAACACCATTGTCACACTCCACA | 8 | 27-49 |
| ACAAACACCATTGTCACACTCCA | 2 | 29-51 |
| CAAACACCATTGTCACACTCCA | 1 | 29-50 |

TABLE 2-continued

Sequences of antisense compounds targeting pri-miR-122a or miR-122a

| Sequence (5' to 3') | SEQ ID NO | Target site on SEQ ID NO: 5 |
|---------------------|-----------|------------------------------|
| GCTATTTAGTGTGATAATGGCGTTTG | 9 | 63-88 |
| GGGAAGGATTGCCTAGCAGT | 10 | 90-109 |
| TTTGATAGTTTAGACACAAA | 11 | 47-66 |
| GTTTGATAGTTTAGACACAAA | 12 | 47-67 |

Table 4 lists antisense compounds having one of the sequences shown in Table 2 and one of the motifs described herein. In Table 4, "Sugar" indicates the sugar type(s) found in the antisense compound; "Backbone" indicates the type of internucleoside linkages; "Motif" indicates the particular motif of the antisense compound. Motifs are described according to the number of nucleosides in each distinct region. For example, the positionally modified motif "5-1-5-1-4-1-6", having 2'-MOE and LNA sugars has a region of 5 2'-MOE modified nucleosides, followed by a region of one LNA modified nucleoside, and so forth. The type of sugar, internucleoside linkage or base modification is noted using the tRNA modification-like abbreviation system. Sequence, internucleoside linkage, nucleobase, and sugar types are all shown and indicated as follows:

Bases in the sequence are indicated with capital letters
   Base modifications are shown before the base residue with a superscripted small letter code (a number can indicate position), and are optional
   Sugar type is shown after the base residue with a subscripted small letter code
   Internucleoside linkage type is shown after the sugar (3'-side) with a subscripted small letter code
   Sugar, nucleobase, and internucleoside abbreviations are shown in Table 3.

TABLE 3

| | Name | Abbreviation |
|---|------|--------------|
| Sugars | 2'-deoxyribose | d |
| | 2'-O-methoxyethyl (MOE) | e |
| | ribose | r |
| | 2'-O-methylribose | m |
| | LNA (Locked Nucleic Acids) | l |
| Nucleobases | adenine | A |
| | cytosine | C |
| | thymine | T |
| | 5-methylcytosine | $^mC$ |
| | guanine | G |
| | uracil | U |
| Internucleoside linkages | phosphodiester | o |
| | phosphorothioate | s |

TABLE 4

Antisense Compounds Targeting a miR-122a nucleic acid

| ISIS Number | SEQ ID NO | Notation (Legend) | Sugar | Backbone | Motif |
|-------------|-----------|-------------------|-------|----------|-------|
| 327895 | 2 | $A_{es}{}^mC_{es}A_{es}A_{es}A_{es}{}^mC_{es}A_{es}{}^mC_{es}{}^mC_{es}$ $A_{es}T_{es}T_{es}G_{es}T_{es}{}^mC_{es}A_{es}{}^mC_{es}A_{es}{}^mC_{es}$ $T_{es}{}^mC_{es}{}^mC_{es}A_e$ | MOE | PS | Uniform |

TABLE 4-continued

Antisense Compounds Targeting a miR-122a nucleic acid

| ISIS Number | SEQ ID NO | Notation (Legend) | Sugar | Back-bone | Motif |
|---|---|---|---|---|---|
| 328372 | 11 | $T_{es}T_{es}T_{es}G_{es}A_{es}T_{ds}A_{ds}G_{ds}T_{ds}T_{ds}$ $A_{ds}G_{ds}A_{ds}{}^mC_{ds}A_{es}{}^mC_{es}A_{es}A_{e}$ | MOE | PS | Gapmer 5-10-5 |
| 328373 | 10 | $G_{es}G_{es}A_{es}A_{es}G_{ds}G_{ds}A_{ds}T_{ds}T_{ds}$ $G_{ds}{}^mC_{ds}{}^mC_{ds}T_{ds}A_{ds}G_{es}{}^mC_{es}A_{es}G_{es}T_{e}$ | MOE and Deoxy | PS | Gapmer 5-10-5 |
| 338654 | 11 | $T_{es}T_{es}T_{es}G_{es}A_{es}T_{es}A_{es}G_{es}T_{es}T_{es}$ $A_{es}G_{es}A_{es}{}^mC_{es}A_{es}{}^mC_{es}A_{es}A_{e}$ | MOE | PS | Uniform |
| 338655 | 10 | $G_{es}G_{es}A_{es}A_{es}G_{es}G_{es}A_{es}T_{es}T_{es}$ $G_{es}{}^mC_{es}{}^mC_{es}T_{es}A_{es}G_{es}{}^mC_{es}A_{es}G_{es}T_{e}$ | MOE | PS | Uniform |
| 339300 | 9 | $G_{do}C_{do}T_{do}A_{do}T_{do}T_{do}T_{do}A_{do}G_{do}T_{do}$ $G_{do}T_{do}G_{do}G_{do}T_{do}A_{do}A_{do}T_{do}G_{do}G_{do}$ $C_{do}G_{do}T_{do}T_{do}T_{do}G_{d}$ | Deoxy | PO | Uniform |
| 342970 | 2 | $A_{ro}C_{ro}A_{ro}A_{ro}A_{ro}C_{ro}A_{ro}C_{ro}C_{ro}A_{ro}U_{ro}$ $U_{ro}G_{ro}U_{ro}C_{ro}A_{ro}C_{ro}A_{ro}C_{ro}U_{ro}C_{ro}C_{ro}$ $A_{r}$ | RNA | PO | Uniform |
| 343160 | 2 | $A_{rs}C_{rs}A_{rs}A_{rs}A_{rs}C_{rs}A_{rs}C_{rs}C_{rs}A_{rs}U_{rs}U_{rs}$ $G_{rs}U_{rs}C_{rs}A_{rs}C_{rs}A_{rs}C_{rs}U_{rs}C_{rs}C_{rs}A_{r}$ | RNA | PS | Uniform |
| 344272 | 1 | ${}^mC_{es}A_{es}A_{es}A_{es}{}^mC_{es}A_{es}{}^mC_{es}{}^mC_{es}A_{es}$ $T_{es}T_{es}G_{es}T_{es}{}^mC_{es}A_{es}{}^mC_{es}A_{es}{}^mC_{es}T_{es}$ ${}^mC_{es}{}^mC_{es}A_{e}$ | MOE | PS | Uniform |
| 344283 | 1 | ${}^mC_{es}A_{es}A_{es}A_{es}{}^mC_{es}A_{ds}mC_{ds}{}^mC_{ds}A_{ds}$ $T_{ds}T_{ds}G_{ds}T_{ds}{}^mC_{ds}A_{ds}{}^mC_{es}A_{es}{}^mC_{es}T_{es}$ ${}^mC_{es}{}^mC_{es}A_{e}$ | MOE | PS | Gapmer 5-10-7 |
| 344294 | 1 | $C_{ro}A_{ro}A_{ro}A_{ro}C_{ro}A_{ro}C_{ro}C_{ro}A_{ro}U_{ro}U_{ro}$ $G_{ro}U_{ro}C_{ro}A_{ro}C_{ro}A_{ro}C_{ro}U_{ro}C_{ro}C_{ro}A_{r}$ | RNA | PO | Uniform |
| 344305 | 1 | $C_{rs}A_{rs}A_{rs}A_{rs}C_{rs}A_{rs}C_{rs}C_{rs}A_{rs}U_{rs}U_{rs}G_{rs}$ $U_{rs}C_{rs}A_{rs}C_{rs}A_{rs}C_{rs}U_{rs}C_{rs}C_{rs}A_{r}$ | RNA | PS | Uniform |
| 345363 | 2 | $A_{es}{}^mC_{es}A_{es}A_{es}A_{es}{}^mC_{ds}A_{ds}{}^mC_{ds}{}^mC_{ds}$ $A_{ds}T_{ds}T_{ds}G_{ds}T_{ds}{}^mC_{ds}A_{es}{}^mC_{es}A_{es}{}^mC_{es}$ $T_{es}{}^mC_{es}{}^mC_{es}A_{e}$ | MOE and DNA | PS | Gapmer 5-10-8 |
| 359606 | 8 | $A_{ro}A_{ro}A_{ro}C_{ro}A_{ro}C_{ro}C_{ro}A_{ro}U_{ro}U_{ro}G_{ro}$ $U_{ro}C_{ro}A_{ro}C_{ro}A_{ro}C_{ro}U_{ro}C_{ro}C_{ro}A_{ro}C_{ro}A_{r}$ | RNA | PO | Uniform |
| 359617 | 8 | $A_{rs}A_{rs}A_{rs}C_{rs}A_{rs}C_{rs}C_{rs}A_{rs}U_{rs}U_{rs}G_{rs}U_{rs}$ $C_{rs}A_{rs}C_{rs}A_{rs}C_{rs}U_{rs}C_{rs}C_{rs}A_{rs}C_{rs}A_{r}$ | RNA | PS | Uniform |
| 365219 | 2 | $A_{eo}{}^mC_{eo}A_{eo}A_{eo}A_{eo}{}^mC_{eo}A_{eo}{}^mC_{eo}{}^mC_{eo}$ $A_{eo}T_{eo}T_{eo}G_{eo}T_{eo}{}^mC_{eo}A_{eo}{}^mC_{eo}A_{eo}{}^mC_{eo}$ ${}^mC_{eo}T_{eo}{}^mC_{eo}{}^mC_{eo}A_{e}$ | MOE | PO | Uniform |
| 365474 | 1 | ${}^mC_{eo}A_{eo}A_{eo}A_{eo}{}^mC_{eo}A_{eo}{}^mC_{eo}{}^mC_{eo}A_{eo}$ $T_{eo}T_{eo}G_{eo}T_{eo}{}^mC_{eo}A_{eo}{}^mC_{eo}A_{eo}{}^mC_{eo}$ $T_{eo}{}^mC_{eo}{}^mC_{eo}A_{e}$ | MOE | PO | Uniform |
| 365660 | 11 | $T_{eo}T_{eo}T_{eo}G_{eo}A_{eo}T_{eo}A_{eo}G_{eo}T_{eo}T_{eo}T_{eo}$ $A_{eo}G_{eo}A_{eo}{}^mC_{eo}A_{eo}{}^mC_{eo}A_{eo}A_{e}$ | MOE | PO | Uniform |
| 386653 | 2 | $A_{ms}C_{ms}A_{ms}A_{ms}A_{ms}C_{ms}A_{ms}C_{ms}C_{ms}$ $A_{ms}U_{ms}U_{ms}G_{ms}U_{ms}C_{ms}A_{ms}C_{ms}A_{ms}$ $C_{ms}U_{ms}C_{ms}C_{ms}A_{m}$ | 2'-O-Methyl | PS | Uniform |
| 386654 | 2 | $A_{mo}C_{mo}A_{mo}A_{mo}A_{mo}C_{mo}A_{mo}C_{mo}C_{mo}$ $A_{mo}U_{mo}U_{mo}G_{mo}U_{mo}C_{mo}A_{mo}C_{mo}A_{mo}$ $C_{mo}U_{mo}C_{mo}C_{mo}A_{m}$ | 2'-O-Methyl | PO | Uniform |
| 387082 | 2 | $A_{es}{}^mC_{es}A_{es}A_{es}A_{es}{}^mC_{ls}A_{es}{}^mC_{es}{}^mC_{es}$ $A_{es}T_{es}T_{ls}G_{es}T_{es}{}^mC_{es}A_{es}{}^mC_{ls}A_{es}{}^mC_{es}$ $T_{es}{}^mC_{es}{}^mC_{es}A_{e}$ | MOE and LNA | PS | Positionally modified 5-1-5-1-4-1-6 |
| 387083 | 2 | $A_{es}{}^mC_{es}A_{es}A_{es}A_{es}{}^mC_{ls}A_{es}{}^mC_{es}{}^mC_{ls}A_{es}$ $T_{es}T_{ls}G_{es}T_{es}{}^mC_{es}A_{es}{}^mC_{ls}A_{es}{}^mC_{es}T_{es}$ ${}^mC_{ls}{}^mC_{es}A_{e}$ | MOE and LNA | PS | Positionally modified 5-1-2-1-2-1-2-1-1-1-3-1-2 |

TABLE 4-continued

Antisense Compounds Targeting a miR-122a nucleic acid

| ISIS Number | SEQ ID NO | Notation (Legend) | Sugar | Back-bone | Motif |
|---|---|---|---|---|---|
| 387574 | 2 | $A_{es}{}^mC_{es}A_{ls}A_{es}{}^mC_{ls}A_{es}{}^mC_{es}{}^mC_{ls}A_{es}$ $T_{es}T_{ls}G_{es}T_{es}{}^mC_{ls}A_{es}{}^mC_{es}A_{ls}{}^mC_{es}T_{es}$ ${}^mC_{ls}{}^mC_{es}A_e$ | MOE and LNA | PS | Positionally modified $(2-1)_7-2$ |
| 387575 | 2 | $A_{eo}{}^mC_{eo}A_{lo}A_{eo}{}^mC_{lo}A_{eo}{}^mC_{eo}{}^mC_{lo}$ $A_{eo}T_{eo}T_{lo}G_{eo}T_{eo}{}^mC_{lo}A_{eo}{}^mC_{eo}A_{lo}{}^mC_{eo}$ $T_{eo}{}^mC_{lo}{}^mC_{eo}A_e$ | MOE and LNA | PO | Positionally modified $(2-1)_7-2$ |
| 387576 | 2 | $A_{es}{}^mC_{es}A_{es}A_{ds}{}^mC_{ds}A_{es}{}^mC_{es}{}^mC_{ds}$ $A_{ds}T_{ds}T_{es}G_{es}T_{ds}{}^mC_{ds}A_{ds}{}^mC_{es}A_{es}{}^mC_{es}$ $T_{es}{}^mC_{es}{}^mC_{es}A_e$ | MOE and Deoxy | PS | Positionally modified 3-3-2-3-2-3-7 |
| 387577 | 2 | $A_{es}{}^mC_{ds}A_{es}A_{ds}{}^mC_{ds}A_{es}{}^mC_{ds}{}^mC_{es}$ $A_{ds}T_{es}T_{ds}G_{es}T_{ds}{}^mC_{es}A_{ds}{}^mC_{es}A_{ds}{}^mC_{es}$ $T_{ds}{}^mC_{es}{}^mC_{ds}A_e$ | MOE and Deoxy | PS | Positionally modified $(1-1)_{11}-1$ |
| 387578 | 2 | $A_{es}{}^mC_{es}A_{es}A_{ds}{}^mC_{ds}A_{es}{}^mC_{es}{}^mC_{ds}$ $A_{ds}T_{ds}T_{es}G_{es}T_{ds}{}^mC_{ds}A_{ds}{}^mC_{es}A_{es}{}^mC_{ds}$ $T_{ds}{}^mC_{ds}{}^mC_{es}A_e$ | MOE and Deoxy | PS | Positionally modified 3-3-2-3-2-3-2-3-2 |
| 387579 | 2 | $A_{ds}{}^mC_{ds}A_{ds}A_{ds}{}^mC_{ds}{}^mC_{es}A_{es}{}^mC_{es}{}^mC_{es}$ $A_{es}T_{es}T_{es}G_{es}T_{es}{}^mC_{es}A_{es}{}^mC_{es}A_{es}{}^mC_{ds}$ $T_{ds}{}^mC_{ds}{}^mC_{ds}A_d$ | MOE and Deoxy | PS | Gapmer 5-13-5 |
| 387580 | 2 | $A_{ds}{}^mC_{ds}A_{ds}A_{ds}{}^mC_{ds}{}^mC_{eo}A_{eo}{}^mC_{eo}{}^mC_{eo}$ $A_{eo}T_{eo}T_{eo}G_{eo}T_{eo}{}^mC_{eo}A_{eo}{}^mC_{eo}A_{eo}{}^mC_{es}$ ${}^mC_{ds}T_{ds}{}^mC_{ds}{}^mC_{ds}A_d$ | MOE and Deoxy | Mixed | Gapmer 5-13-5 |
| 387581 | 2 | $A_{es}{}^mC_{es}A_{es}A_{ls}A_{es}{}^mC_{es}A_{es}{}^mC_{ls}{}^mC_{es}A_{es}$ $T_{es}T_{ls}G_{es}T_{es}{}^mC_{es}A_{ls}{}^mC_{es}A_{es}{}^mC_{es}T_{ls}$ ${}^mC_{es}{}^mC_{es}A_e$ | MOE and LNA | PS | Positionally modified $(3-1)_5-3$ |
| 387582 | 2 | $A_{es}{}^mC_{es}A_{ls}A_{es}A_{es}{}^mC_{ls}A_{ds}{}^mC_{ds}{}^mC_{ls}A_{es}$ $T_{es}T_{ls}G_{ds}T_{ds}{}^mC_{ds}A_{es}{}^mC_{es}A_{ls}{}^mC_{es}T_{es}$ ${}^mC_{ls}{}^mC_{es}A_e$ | Deoxy, MOE and LNA | PS | Positionally modified |
| 387583 | 2 | $A_{es}{}^mC_{es}A_{es}A_{ds}A_{ds}{}^mC_{es}A_{es}{}^mC_{ds}{}^mC_{ds}$ $A_{ds}T_{es}T_{es}G_{ds}T_{ds}{}^mC_{ds}A_{ds}{}^mC_{es}A_{es}{}^mC_{es}$ $T_{es}{}^mC_{es}{}^mC_{es}A_e$ | MOE and Deoxy backbone | PS | Positionally modified 3-2-2-3-2-2-8 |
| 387584 | 2 | $A_{es}{}^mC_{es}A_{es}A_{es}A_{es}{}^mC_{ds}A_{ds}{}^mC_{es}{}^mC_{es}$ $A_{ds}T_{ds}T_{ds}G_{es}T_{es}{}^mC_{ds}A_{ds}{}^mC_{ds}A_{es}{}^mC_{es}$ $T_{es}{}^mC_{es}{}^mC_{es}A_e$ | MOE and Deoxy | PS | Positionally modified 5-2-2-3-2-3-5 |
| 392885 | 2 | $A_{es}C_{es}A_{es}A_{es}A_{es}C_{es}A_{es}C_{es}C_{es}A_{es}$ $U_{es}U_{es}G_{es}U_{es}C_{es}A_{es}C_{es}A_{es}C_{es}U_{es}$ $C_{es}C_{es}A_e$ | MOE | PS | Uniform |
| 392886 | 2 | $A_{es}C_{es}A_{eo}A_{eo}A_{eo}C_{eo}A_{eo}C_{eo}C_{eo}A_{eo}$ $U_{eo}U_{eo}G_{eo}U_{eo}C_{eo}A_{eo}C_{eo}A_{eo}C_{eo}U_{es}$ $C_{es}C_{es}A_e$ | MOE | MIXED | Uniform |
| 392891 | 2 | $A_{ms}C_{ms}A_{mo}A_{mo}A_{mo}C_{mo}A_{eo}C_{mo}C_{mo}$ $A_{mo}U_{mo}U_{mo}G_{mo}U_{mo}C_{mo}A_{mo}C_{eo}A_{eo}$ $C_{mo}U_{ms}C_{ms}C_{es}A_m$ | MOE and 2'-O-Methyl | MIXED | Positionally modified 6-1-9-2-3-1-1 |
| 393132 | 2 | $A_{es}{}^mC_{es}A_{eo}A_{eo}A_{eo}{}^mC_{eo}A_{es}{}^mC_{eo}{}^mC_{eo}$ $A_{eo}T_{eo}T_{eo}G_{eo}T_{eo}{}^mC_{eo}A_{eo}{}^mC_{eo}A_{eo}$ ${}^mC_{eo}T_{es}{}^mC_{es}{}^mC_{es}A_e$ | MOE | MIXED | Uniform |
| 393205 | 2 | $A_{ms}{}^mC_{ms}A_{ms}A_{ms}A_{ms}{}^mC_{ms}A_{ms}{}^mC_{ms}$ ${}^mC_{ms}A_{ms}T_{ms}T_{ms}G_{ms}T_{ms}{}^mC_{ms}A_{ms}$ ${}^mC_{ms}A_{ms}{}^mC_{ms}T_{ms}{}^mC_{ms}{}^mC_{ms}A_m$ | 2'-O-Methyl | PS | Uniform |
| 393833 | 2 | $A_{ms}C_{ms}A_{mo}A_{mo}A_{mo}C_{mo}A_{mo}C_{mo}C_{mo}$ $A_{mo}U_{mo}U_{mo}G_{mo}U_{mo}C_{mo}A_{mo}C_{mo}A_{mo}$ $C_{mo}U_{ms}C_{ms}C_{ms}A_m$ | 2'-O-Methyl | MIXED | Uniform |
| 396604 | 2 | $A_{ds}{}^mC_{ds}A_{ls}A_{ds}A_{ds}{}^mC_{ls}A_{ds}{}^mC_{ds}{}^mC_{ls}$ $A_{ds}T_{ds}T_{ds}G_{ds}T_{ds}{}^mC_{ls}A_{ds}{}^mC_{ds}A_{ls}$ ${}^mC_{ds}T_{ds}{}^mC_{ls}{}^mC_{ds}A_d$ | MOE and LNA | PS | Positionally modified $(2-1)_7-2$ |

TABLE 4-continued

Antisense Compounds Targeting a miR-122a nucleic acid

| ISIS Number | SEQ ID NO | Notation (Legend) | Sugar | Backbone | Motif |
|---|---|---|---|---|---|
| 396605 | 2 | $A_{ms}{}^mC_{ms}A_{ls}A_{ms}A_{ms}{}^mC_{ls}A_{ms}{}^mC_{ms}$ ${}^mC_{ls}A_{ms}T_{ms}T_{ls}G_{ms}T_{ms}{}^mC_{ls}A_{ms}{}^mC_{ms}$ $A_{ls}{}^mC_{ms}T_{ms}{}^mC_{ls}{}^mC_{ms}A_m$ | 2'-O-Methyl and LNA | PS | Positionally modified $(2-1)_7-2$ |

TABLE 5

Truncated antisense compounds targeting miR-122a: uniformly modified with 2'-MOE and phosphorothioate linkages

| ISIS # | SEQUENCE | SEQ ID NO | Target site on SEQ ID NO: 5 | # Truncated nucleosides | Position of truncation |
|---|---|---|---|---|---|
| 386655 | ACAAACACCATTGTCACACTC | 13 | 31-51 | 2 | 3' |
| 386656 | ACAAACACCATTGTCACAC | 14 | 33-51 | 4 | 3' |
| 386657 | ACAAACACCATTGTCAC | 15 | 35-51 | 6 | 3' |
| 386658 | AAACACCATTGTCACACTCCA | 16 | 29-49 | 2 | 5' |
| 386659 | ACACCATTGTCACACTCCA | 17 | 29-47 | 4 | 5' |
| 386660 | ACCATTGTCACACTCCA | 18 | 29-45 | 6 | 5' |

TABLE 6

Mismatched antisense compounds targeting miR-122a: uniformly modified with 2'-MOE and phosphorothioate linkages

| ISIS # | SEQUENCE | SEQ ID NO | Sugar | Backbone | Motif |
|---|---|---|---|---|---|
| 386661 | ACATACACCATTGTCACAGTCCA | 19 | MOE | PS | Uniform |
| 386662 | ACATACACCATTGTCACACTCCA | 20 | MOE | PS | Uniform |
| 386663 | ACATACACCATTCTCACAGTCCA | 21 | MOE | PS | Uniform |
| 386664 | ACATACACCTTTCTCACAGTCCA | 22 | MOE | PS | Uniform |
| 386665 | ACATACACCTTTCTCAGAGTCCA | 23 | MOE | PS | Uniform |
| 386666 | ACATACTCCTTTCTCAGAGTCCA | 24 | MOE | PS | Uniform |

ISIS 343160 is an oligomeric compound representing a chemically modified miR-122a mimic. It is also understood that the human miR-122a mimic compound may also mimic other mRNAs from mammals, such as those from rodent species, for example. It is also understood that these mimics can serve as the basis for several variations of nucleic acid oligomeric compounds, including compounds with chemical modifications such as uniform or chimeric 2'-MOE oligomeric compounds, as well as LNAs and PNAs; such oligomeric compounds are also within the scope of the invention.

Example 4

Effects of Antisense Compounds Targeting miR-122a in Phenotypic Assays

The effects of antisense oligonucleotides ISIS 328372, ISIS 328373, and ISIS 327895 on miR-122a were tested in several phenotypic assays, including an apoptosis assay, an adipocyte differentiation assay, and an insulin signaling assay. The experimental details of these assays, and the results obtained, are described in detail in U.S. Application Publication No. 2005/0261218, which is hereby incorporated by reference in its entirety. As described therein, ISIS 328372 and ISIS 328373 did not induce apoptosis in the apoptosis assay. ISIS 327895 reduced levels of markers of adipocyte differentiation, and decreased mRNA expression of follistatin and PEPCKc in the insulin signaling assay.

Example 5

Modulation of miR-122a Activity In Vitro with Antisense Compounds

To monitor inhibition of miR-122a with antisense oligonucleotides, regulation of several computationally predicted miR-122a targets was assayed in vitro.

Mouse primary hepatocytes were isolated from Balb/c mice using methods described in the art (Neufeld, 1997, Methods Mol. Biol., 75:145-151.). Cells were seeded into 96-well plates in culture medium (Williams' Medium E supplemented with 10% fetal bovine serum, 10 nM HEPES, and penicillin/streptomycin) and cultured overnight before transfection. Transfection of oligonucleotide in LIPOFECTIN® (Invitrogen, Carlsbad, Calif.) was performed in triplicate, according to the manufacturer's instructions. Cells were treated with either ISIS 327895 or the control oligonucleotide ISIS 342683 at concentrations of 15 nM, 44 nM, or 133 nM. Cells were lysed 24 hours after transfection and total RNA was harvested using QIAGEN® RNEASY® 96 columns on a BIOROBOT®V 3000 (Qiagen, Valencia, Calif.).

The mRNA levels of miR-122a target genes predicted by the TargetScan algorithm (Lewis et al, 2005, Cell, 120: 15-20; Lewis et al., 2003, Cell, 115:787-798) were measured using primer probe sets designed to hybridize to each particular predicted target gene and routine TAQMAN® real-time PCR methods. The predicted target mRNAs examined are shown in Table 7. Also shown in Table 7 are GENBANK® accession numbers associated with the mouse and human target mRNAs.

TABLE 7 miR-122a target genes predicted by the TargetScan algorithm

| Gene name | Abbreviation | Mouse GENBANK ® accession number | Human GENBANK ® accession number |
| --- | --- | --- | --- |
| Glycogen synthase 1 (muscle) | GYS1 | NM_008195.1 | NM_002103.3 |
| solute carrier family 7 (cationic amino acid transporter, y+ system), member 1 | SLC7A1 or CAT-1 | NM_003045.3 | NM_007513.1 |
| misshapen-like kinase 1 (zebrafish) | MINK1 | NM_016713.1 | NM_015716.2 |
| aldolase A, fructose-bisphosphate | ALDOA | NM_000034.1 | NM_007438.3 |
| Cyclin G | CCNG1 | NM_004060.3 | NM_009831.1 |
| procollagen-proline, 2-oxoglutarate 4-dioxygenase (proline 4-hydroxylase), alpha polypeptide I | P4HA1 | NM_011030.1 | NM_000917.1 |

Five of the targets (GYS1, SLC7A1, ALDOA, CCNG1, P4HA1) were upregulated 1.5 to 3 fold after treatment with ISIS 327895, while none were affected by treatment with the control oligonucleotide. Only the predicted MINK1 (referred to as mMINK in Figures) target was unaffected after treatment with ISIS 327895.

In a reciprocal experiment, treatment of the mouse liver carcinoma AML12 cell line with a miR-122a mimetic caused inhibition of GYS1, SLC7A1/CAT-1, and ALDOA, as assayed by real-time PCR. The miR-122a duplex RNA that was used as a miR-122a mimetic was purchased from Dharmacon (Lafayette, Colo.). The miR-122a duplex contained: UGGAGUGUGACAAUGGUGUUUGU (SEQ ID NO: 3) and its complement AAACACCAUUGUCACACUCCAUA (SEQ ID NO: 25). The 5' mismatch miR-122a duplex comprised: UGCACAGAGACAAUGGUGUUUGU (SEQ ID NO: 26) and its complement AAACACCAUUGUCUCUGUGCAUA (SEQ ID NO: 27). The 3' mismatch miR-122a duplex comprise UGGAGUGUGACAWUGCAGUAGUG (SEQ ID NO: 28) and its complement AUACUGCAAUGUCACACUCCAUA (SEQ ID NO: 29). AML12 cells do not have high expression levels of miR-122a as are observed in primary hepatocytes (see FIG. 6). Transfection of the miR-122a mimic led to a decrease in mRNA levels for the same 5 targets (GYS1, SLC7A1, ALDOA, CCNG1, P4HA1) that were upregulated following antisense inhibition of miR-122a. Interestingly, the miR-122a mimetic did not modulate expression of MINK or NPEPPS, showing that in vitro antisense and miR mimetic effects on miR-122a target genes correlate.

Example 6

Modulation of miR-122a Activity In Vitro with mRNA Antisense

To monitor inhibition of miR-22a with antisense oligonucleotides bearing varied modifications, regulation of the predicted miR-122a target GYS1 was assayed in mouse primary hepatocytes, using real-time PCR methods as described herein. Cells were treated with ISIS 327895, ISIS 365219, ISIS 386653, ISIS 386654, ISIS 345363, or the control oligonucleotide ISIS 342683 at doses of 15 nM, 44 nM, 133 nM, or 400 nM. The sequence of ISIS 342683 is CCTTCCCT-GAAGGTTCCTCCTT (SEQ ID NO: 30); this oligomeric compound is uniformly composed of 2'-MOE nucleosides, has a phosphorothioate backbone, and all cytosines are 5-methylcytosines. ISIS 327895 and ISIS 365219 were effective in inhibiting miR-122a, as evidenced by the increased expression of GYS1. ISIS 386653 and ISIS 386654 increased GYS1 mRNA levels to a lesser extent. The gapmer ISIS 345363 did not markedly increase GYS1 mRNA levels.

Similar experiments suggested that of six predicted miR-122a target genes tested (GYS1, SLC7A1, ALDO A, CCNG1, MINK, P4HA1), mMINK is not modulated by antisense oligonucleotides targeting miR-122a. However, mCAT-1 does appear to be modulated by targeting miR-122a.

To examine the effects of oligonucleotides of varying lengths on miR-122a inhibition, regulation of the predicted miR-122a target GYS1 was assayed in mouse primary hepatocytes, using methods as described herein. Cells were treated with ISIS 386655, ISIS 386656, ISIS 386657, ISIS 386658, ISIS 386659, or ISIS 386660 at doses of 15 nM, 44 nM, 133 nM, or 400 nM. While truncations resulted in slightly less stimulation of GYS1 mRNA levels, some truncated antisense compound were able to stimulate GYS1 mRNA expression. Antisense compounds in which 2, 4, or 6 nucleosides were truncated from the 5' end, in this assay, were able to stimulate GYS1 mRNA expression, relative to control samples. An antisense compound in which 2 nucleosides were truncated from the 3' end was able to stimulate GYS1 mRNA expression, relative to control samples. However, truncations of 4 or 6 nucleosides from the 3' end significantly reduced the ability of the antisense compounds to stimulate GYS1 mRNA expression.

To examine the effects of mismatches on the ability of oligonucleotides targeted to miR-122a to inhibit its effects on the predicted target GYS1, mouse primary hepatocytes were treated with oligonucleotides bearing mismatches to miR-122a (ISIS 386661, ISIS 386662, ISIS 386663, ISIS 386664, ISIS 386665, and ISIS 386666). Increasing the number of mismatches appears to decrease the ability of the antisense oligonucleotides to modulate GYS1 mRNA levels. One mismatch was tolerated; however, 2 mismatches resulted in only a slight increase in GYS1 mRNA levels, whereas 3 to 6 mismatches completely ablated miR-122a antisense oligonucleotide activity.

Embodiments of the present invention include methods of validating predicted miR-122a targets. Also provided are methods of modulating miR-122a targets with an antisense compound which targets miR-122a. In one embodiment, the antisense compound has the nucleobase sequence of SEQ ID NO: 2. In another embodiment, the antisense compound is uniformly comprised of 2'-MOE sugar modifications. In another embodiment, the antisense compound is ISIS 327895. Further provided are methods of assaying for inhibition of miR-122a comprising monitoring expression of a miR-122a target gene.

Example 7

Modulation of miR-122a activity in vivo with mRNA Antisense-Normal Mice

Male C57BL/6 mice were obtained from The Jackson Laboratory. The mice were separated into treatment groups and were treated intraperitoneally with doses of ISIS 327895 ranging from 12.5 to 75 mg/kg or with 75 mg/kg of the control oligonucleotide ISIS 342683 twice weekly for four weeks. Mice treated with saline alone served as further controls. The mice appeared healthy and normal at the end of treatment with plasma AST and ALT levels in the normal range and no loss of body weight or reduced food intake. Histological analysis of liver sections revealed no apparent change in morphology. (Histological analysis of liver was carried out via routine procedures known in the art. Briefly, liver was fixed in 10% buffered formalin and embedded in paraffin wax. 4-mm sections were cut and mounted on glass slides. After dehydration, the sections were stained with hematoxylin and eosin.)

The levels of the five miR-122a target mRNAs identified in vitro were evaluated in liver tissue using Taqman real-time PCR. Four of the five mRNAs (GYS1, ALDOA, P4HA1, and CCNG1) were increased in the mice treated with ISIS 327895, while no target mRNA changes were observed in mice treated with the control oligonucleotide, demonstrating specific inhibition of miR-122a in the liver. P4HA1 displayed maximal upregulation at the lowest dose of ISIS 327895 tested. An embodiment of the present invention is a method of modulating miR-122a targets in an animal comprising administering an antisense oligonucleotide targeting miR-122a. In one embodiment, the targets are modulated in the liver. In one embodiment, said antisense oligonucleotide is ISIS 327895.

Northern blotting for miR-122a in liver RNA from the treated mice revelaed a three-fold reduction in miR-122a levels after treatment with the lowest dose (12.5 mg/kg) of ISIS 327895 and a reduction of greater than 10-fold at the highest (75 mg/kg) dose, but the control oligonucleotide had no effect on miR-122a levels in the liver. An embodiment of the present invention is a method of reducing miR-122a levels in the liver of an animal comprising administering an antisense oligonucleotide targeting miR-122a. In one embodiment, said antisense oligonucleotide is ISIS 327895.

Plasma levels of total cholesterol, triglycerides and glucose were also monitored using methods known in the art (for example, via Olympus AU400e automated clinical chemistry analyzer, Melville, N.Y.). After four weeks of treatment, inhibition of miR-122a with ISIS 327895 did not significantly affect plasma glucose levels, however, significant reductions in total cholesterol and triglycerides were observed at all doses tested as compared to saline or control-oligonucleotide treated mice.

Embodiments of the present invention include methods of reducing serum cholesterol, glucose, or triglycerides in an animal comprising administering an antisense compound targeted to miR-122a. In one embodiment, the antisense compound has the nucleobase sequence of SEQ ID NO: 2. In another embodiment, the antisense compound is uniformly comprised of 2'-MOE sugar modifications. In another embodiment, the antisense compound is ISIS 327895.

Example 8

Effects of miR-122a antisense oligonucleotide treatment in a diet-induced model of obesity: 25 mg/week study Male, C57bl/6 mice, 6-7 weeks old, were fed a high fat diet (60% kcal from fat) for 19 weeks prior to beginning treatment with antisense oligonucleotides. Mice were fed ad libitum. Starting insulin levels were approximately 15 ng/dL and body composition was approximately 20% fat. Mice were dosed subcutaneously at 12.5 mg/kg twice weekly (i.e. 25 mg/wk), for a total of 11 total doses. Each treatment group consisted of 5 mice.

Treatment groups were as follows: saline; ISIS 327895, antisense to miR-122a; ISIS 342683, a scrambled control oligonucleotide. The sequence of ISIS 342683 is CCTTC-CCTGAAGGTTCCTCCTT (SEQ ID NO: 30); this oligomeric compound is uniformly composed of 2'-MOE nucleosides, has a phosphorothioate backbone, and all cytosines are 5-methylcytosines.

Body composition was determined by MRI at the start of the study and following 3.5 and 5 weeks of treatment. Serum chemistries were analyzed following 2, 3, 4, 5, and 6 weeks of treatment. Insulin was measured via routine ELISA in the fed state following 3 weeks of treatment, and in the fasted state following 5 weeks of treatment. An oral glucose tolerance test was performed following 5 weeks of treatment (via routine procedures: glucose was administered, blood samples were collected and analyzed on a clinical analyzer).

Serum lipoprotein and cholesterol profiling was performed as described (Kieft et al., 1991) using a Beckman System Gold 126 HPLC system, a 507e refridgerated autosampler, a 126 photodiode array detector (Beckman Instruments) and a Superose 6 HR 10/30 column (Pfizer). HDL, LDL, and VLDL fractions were measured at a wavelength of 505 nm and valiated with a cholesterol calibration kit (Sigma, St. Louis, Mo.). For each experiment, a three-point standard curve was performed in triplicate to determine the absolute concentration of each lipoprotein fraction. Lipoprotein analysis performed in this manner showed that the decrease in total cholesterol reflected a reduction in both low-density lipoprotein and high-density lipoprotein fractions.

Glycogen synthase 1 is a miR-122a target and its expression is modulated by antisense inhibition of miR-122a. As glycogen synthase 1 expression was elevated in livers of mice treated with ISIS 327895, glycogen content in livers was evaluated. A significant increase in glycogen levels in the livers of the ISIS 327895-treated mice was observed, suggesting that miR-122a may also regulate glycogen storage through its repression of the muscle glycogen synthase (GYS1) mRNA. Mean insulin levels are shown in Table 8. Serum chemistry analysis is shown in Table 9.

TABLE 8

Mean insulin levels in 25 mg/wk DIO Study

|  | Week 3 | Week 5 (fasted) | Week 6 |
|---|---|---|---|
| Saline | 39 | 3 | 22 |
| miR-122a(uniform MOE) - 327895 | 14 | 6 | 8 |
| Uniform MOE 141923-342683 | 25 | 3 | 10 |

Histological analysis of the liver showed substantial reduction of liver steatosis with ISIS 327895 treatment. Liver triglyceride levels were also reduced with antisense inhibition of miR-122a. Liver weights were also decreased. A trend toward reduction in plasma transaminase levels in ISIS 327895-treated mice indicates an improvement in hepatic function. These changes also correlated with a reduction in mRNA levels of key enzymes FASN, ACC2, and SCD1.

A slight lowering of food consumption was observed in the mice treated with ISIS 327895. Cholesterol was lowered by approximately 35% following 2 weeks of treatment and by about 40% at the end of the study. Following 4 weeks of treatment, HDL was decreased by 50% and LDL was decreased by 28%. Consistent with the observed cholesterol reduction, levels of ApoB-100 protein in the plasma of ISIS 327895-treated mice were reduced compared to saline-treated mice, as measured by Western blotting. No significant

TABLE 9

Mean serum chemistry levels in 25 mg/wk DIO Study.

|  |  | GLUC | ALT | AST | CHOL | TRIGS | HDL | LDL |  |
|---|---|---|---|---|---|---|---|---|---|
| Pre-dosing | Saline | 231 | 48 | 68 | 190 | 89 | 150 | 18 |  |
|  | 327895 (miR-122a) | 258 | 50 | 61 | 180 | 96 | 141 | 17 |  |
|  | 342683 Uniform MOE 141923 | 250 | 79 | 77 | 215 | 81 | 167 | 17 |  |
|  | Saline - Normal Chow | 188 | 22 | 54 | 66 | 82 | 52 | 10 |  |

|  |  | Gluc | ALT | AST | CHOL | HDL | LDL | TRIGS | NEFA |
|---|---|---|---|---|---|---|---|---|---|
| 2 weeks | Saline | 223 | 69 | 69 | 209 | 163 | 24 | 86 | 0.518 |
|  | miR-122a(uniform MOE)-327895 | 234 | 83 | 54 | 135 | 103 | 17 | 80 | 0.480 |
|  | Uniform MOE 141923-342683 | 218 | 117 | 77 | 225 | 178 | 26 | 84 | 0.568 |
|  | Saline - Normal Chow | 167 | 28 | 47 | 63 | 47 | 10 | 80 | 0.660 |

|  |  | GLUC | ALT | AST | CHOL | HDL | LDL | TRIG |  |
|---|---|---|---|---|---|---|---|---|---|
| 3 weeks | Saline | 261 | 89 | 83 | 208 | 162 | 27 | 91 |  |
|  | miR-122a(uniform MOE)-327895 | 214 | 71 | 48 | 136 | 102 | 21 | 81 |  |
|  | Uniform MOE 141923-342683 | 236 | 107 | 71 | 216 | 167 | 31 | 83 |  |
|  | Saline - Normal Chow | 170 | 36 | 57 | 60 | 44 |  | 88 |  |

|  |  | GLUC | ALT | AST | CHOL | HDL | LDL | TRIG | NEFA |
|---|---|---|---|---|---|---|---|---|---|
| 4 weeks | Saline | 184 | 77 | 78 | 206 | 156 | 28 | 99 | 0.836 |
|  | miR-122a(uniform MOE)-327895 | 204 | 74 | 51 | 125 | 76 | 20 | 74 | 0.616 |
|  | Uniform MOE 141923-342683 | 242 | 131 | 89 | 226 | 177 | 29 | 69 | 0.744 |

|  |  | GLUC | ALT | AST | CHOL | TRIG |  |  | NEFA |
|---|---|---|---|---|---|---|---|---|---|
| 5 weeks | Saline | 222 | 159 | 135 | 195 | 94 |  |  | 1 |
|  | miR-122a(uniform MOE)-327895 | 207 | 89 | 86 | 122 | 79 |  |  | 1 |
|  | Uniform MOE 141923-342683 | 189 | 231 | 165 | 209 | 87 |  |  | 1 |

|  |  | GLUC | ALT | AST | CHOL | HDL | LDL | TRIG |  |
|---|---|---|---|---|---|---|---|---|---|
| 6 weeks | Saline | 180 | 94 | 100 | 220 | 174 | 27 | 94 |  |
|  | miR-122a(uniform MOE)-327895 | 188 | 47 | 52 | 135 | 97 | 21 | 94 |  |
|  | Uniform MOE 141923-342683 | 219 | 129 | 124 | 223 | 178 | 27 | 76 |  |

GLUC = glucose; ALT = alanine aminotransferase; AST = aspartate aminotransferase; chol = total cholesterol; trigs = triglycerides; HDL = HDL-cholesterol; LDL = LDL-cholesterol; NEFA = non-esterified fatty acids miR-122a target genes whose expression is upregulated following antisense inhibition of miR-122a in vivo included GYS1, ALDO A, CCNG1, and P4HA1. mRNA levels were measured by real-time PCR using procedures described herein and commonly known in the art. Upregulation of these genes in mice treated with ISIS 327895 confirms inhibition of miR-122a activity.

changes in glucose, serum transaminases, body composition or food consumption were observed. Slight changes in FFA and serum triglycerides were observed. Changes were observed in insulin levels as shown in Table 8. Treatment with ISIS 327895 slightly increased liver glycogen levels.

Embodiments of the present invention include methods of improving insulin sensitivity, methods of reducing cholesterol, methods of reducing LDL cholesterol, methods of reducing FFA, methods of reducing ApoB-100 levels, and methods of reducing triglycerides in the serum of an animal by administering an antisense compound targeted to miR-122a. In a further embodiment, improvement in insulin sensitivity is measured as a reduction in circulating insulin levels. In one embodiment, the antisense compound has the nucleobase sequence of SEQ ID NO: 2. In another embodiment, the antisense compound is uniformly comprised of 2'-MOE sugar modifications. In a further embodiment, the antiense compound is ISIS 327895.

Example 9

Gene Expression Changes Following antisense inhibition of miR-122a

In one embodiment, changes in liver gene expression following antisense inhibition of miR-122a were evaluated by microarray analysis. Liver RNA was isolated from normal mice treated with 50 mg/kg of ISIS 327895 twice weekly and from animals treated with saline alone, and microarray analysis was performed. GE CODELINK™ Mouse Whole Genome Bioarrays were used according to the manufacturer's protocols. Analysis of modulated genes by Gene Ontology category revealed that many genes involved in regulation of lipid and carbohydrate metabolism were affected in the ISIS 327895 treated mice. Key enzymes in the fatty acid synthesis pathway, cholesterol biosynthesis pathway, acetyl CoA transport pathway, and glycolysis pathway were inhibited. Phosphomevalonate kinase (PMVK) mRNA downregulation was statistically significant. Several other genes related to cholesterol metabolism were also reduced, including HMGCR and PMVK. Several key genes known to regulate fatty acid synthesis and oxidation, including ACC1, ACC2, ACLY, SCD1 and FASN, were significantly downregulated in the microarray experiment, and the downregulation of these 5 genes was confirmed by real-time PCR.

Many of the upregulated genes show enriched expression in brain, fertilized eggs, and placenta. Genes indicative of hepatocyte de-differentiation, for example, HNF-1alpha, HNF-1beta, HNF-4, albumin, cytokeratin 19, and alpha-fetoprotein, did not exhibit altered expression following antisense inhibition of miR-122a. The microarray data is deposited in a publicly accessible database Gene Expression Omnibus (GEO) with series accession GSE3603 and are herein incorporated by reference.

Although the microarray experiment was designed primarily to uncover the downstream effects of miR-122a inhibition after chronic treatment, rather than identify direct miR-122a target genes, 108 significantly upregulated genes with a strict 7 or 8 nucleoside seed match in their 3, UTR were identified. These may be direct miR-122a target genes. Most of these mRNAs were modestly increased by only 1.5-3-fold. These genes are identified in the following table (Table 10) by their GENBANK® accession numbers and the associated gene symbol. Also indicated is whether the target includes a 7 or 8 nucleoside seed.

TABLE 10

Target gene expression profile following antisense inhibition of miR-122a in vivo

| Accession Number | Gene Symbol | Has Seed of 7 | Has Seed of 8 |
|---|---|---|---|
| NM_009834 | Ccrn41 | yes | |
| NM_007438 | Aldoa | yes | yes |
| NM_198626 | AI480653 | yes | yes |
| NM_021534 | Pxmp4 | yes | yes |
| XM_358753; XM_622593 | 1500031H01Rik | yes | |
| NM_029802 | Arfip2 | yes | |
| NM_033595 | Pcdhga12 | yes | yes |
| XM_484912 | LOC545361 | yes | yes |
| NM_009739 | Bckdk | yes | yes |
| NM_026404 | Slc35a4 | yes | |
| NM_019722 | Arl2 | yes | |
| NM_175935 | G6pc3 | yes | |
| NM_007794; NM_181322 | Ctcf | yes | |
| XM_149022 | 9630037P07Rik | yes | |
| NM_011039 | Pax7 | yes | |
| NM_134044 | AI413782 | yes | |
| NM_019637 | Styx | yes | yes |
| NM_134023 | Tbc1d10a | yes | yes |
| NM_031999 | Tm7sf1 | yes | |
| NM_019580 | MGI: 1891827 | yes | |
| NM_028162 | Tbc1d5 | yes | yes |
| NM_027901 | Gtf3c2 | yes | |
| XM_144076 | Lrrc38 | yes | |
| NM_011825 | Grem2 | yes | yes |
| NM_181422 | Pkd2l1 | yes | |
| NM_013865 | Ndrg3 | yes | yes |
| NM_019701 | Clcnkb | yes | yes |
| NM_030678 | Gys1 | yes | yes |
| NM_010148 | Epn2 | yes | |
| NM_172741 | 4931406P16Rik | yes | yes |
| NM_027867 | Brmsl1 | yes | |
| NM_010544 | Ihh | yes | yes |
| XM_124695 | LOC231914 | yes | yes |
| NM_027712; NM_177639 | Dlgap1 | yes | |
| NM_153536 | B130050I23Rik | yes | yes |
| NM_145587 | Sbk1 | yes | yes |
| NM_001029912 | Zswim5 | yes | yes |
| XM_355846 | 2210411K11Rik | yes | |
| NM_146012 | Ctdsp2 | yes | yes |
| NM_177591; NM_177915; NM_183335; NM_183336 | Igsf1 | yes | yes |
| XM_132396 | A930033C01Rik | yes | yes |
| NM_008270 | Hoxb9 | yes | |
| NM_080446 | Helb | yes | |
| NM_146221 | Zfp426 | yes | |
| NM_172870 | Bnc2 | yes | yes |
| NM_177165 | F630111L10Rik | yes | |
| NM_025799 | Fuca2 | yes | yes |
| NM_133236; NM_178072 | Glcci1 | yes | |
| NM_019805 | Anapc7 | yes | yes |
| XM_133245 | Lypd5 | yes | |
| NM_022023 | Gmfb | yes | yes |
| NM_011099 | Pkm2 | yes | yes |
| NM_138954 | Rfp14 | yes | yes |
| NM_011049 | Pctk1 | yes | yes |
| NM_172862 | Frem2 | yes | |
| NM_020505; NM_146139 | Vav3 | yes | |
| NM_028940 | 4933402J24Rik | yes | |
| XM_127565 | Flnb | yes | yes |
| NM_008942 | Npepps | yes | yes |
| NM_022305 | B4galt1 | yes | yes |
| NM_177041 | Flad1 | yes | |
| NM_025675 | 5730421E18Rik | yes | |
| NM_133886 | AU040320 | yes | |
| NM_175268; NM_212473 | A930008G19Rik | yes | yes |
| XM_619711 | Cdc42bpa | yes | |
| NM_172054 | Txndc9 | yes | yes |
| NM_019921 | Akap10 | yes | yes |
| NM_146175 | Zfp282 | yes | |
| NM_028013 | 2310067E08Rik | yes | yes |
| NM_178111 | Trp53inp2 | yes | yes |
| NM_007399 | Adam10 | yes | |
| NM_019421 | Cd320 | yes | |

TABLE 10-continued

Target gene expression profile following antisense
inhibition of miR-122a in vivo

| Accession Number | Gene Symbol | Has Seed of 7 | Has Seed of 8 |
|---|---|---|---|
| NM_175263 | 5730593N15Rik | yes | |
| NM_146016 | C230094A16Rik | yes | |
| NM_153799 | AA517853 | yes | |
| NM_009737 | Bcat2 | yes | yes |
| NM_198615 | Rkhd1 | yes | yes |
| NM_010547; NM_178590 | Ikbkg | yes | yes |
| NM_019972 | Sort1 | yes | |
| NM_001025378; NM_008765 | Orc2l | yes | yes |
| XM_131700 | BC039093 | yes | |
| NM_027266 | Rg9mtd3 | yes | |
| XM_203393 | Prr6 | yes | |
| NM_172827 | Lnpep | yes | yes |
| XM_489246 | 1810019D21Rik | yes | |
| NM_172564 | Tns4 | yes | yes |
| XM_485010 | 2510042P03Rik | yes | |
| NM_146163 | Myo1h | yes | yes |
| NM_016696 | Gpc1 | yes | yes |
| NM_025472 | 1810032O08Rik | yes | |
| NM_198026 | Iqcc | yes | yes |
| NM_181399 | Usp6nl | yes | |
| NM_025788 | Btbd14b | yes | yes |
| NM_021491 | Smpd3 | yes | yes |
| NM_175201 | Rnf38 | yes | |
| NM_010692 | Lbx2 | yes | yes |
| NM_175268; NM_212473 | A930008G19Rik | yes | yes |
| NM_030138 | Centb2 | yes | yes |
| NM_172570 | Trim47 | yes | yes |
| XM_619260 | Ppp2r2a | yes | |
| NM_027480 | Ankrd24 | yes | yes |
| NM_028058 | Fundc1 | yes | |
| NM_010921 | Nkx3-1 | yes | yes |
| NM_178119 | Centg2 | yes | |
| XM_619141 | B230112C05Rik | yes | yes |
| NM_146175 | Zfp282 | yes | |
| NM_019437 | Rfk | yes | |
| XM_618754 | LOC544690 | yes | |

Therefore, another embodiment of the present invention is a method of identifying miR-122a targets. Another embodiment of the present invention is a method of modulating the expression of any of the 108 targets identified in the preceding table comprising modulating the miR-122a. In a particular embodiment, miR-122a is modulated by an antisense compound. In one embodiment, the antisense compound has the nucleobase sequence of SEQ ID NO: 2. In another embodiment, the antisense compound is uniformly comprised of 2'-MOE sugar modifications. In a further embodiment, the antiense compound is ISIS 327895.

Example 10

Modulation of Lipid Metabolism Following Antisense Inhibition of miR-122a

Fatty acid oxidation is an ATP-producing catabolic pathway. The central metabolic sensor AMPK is a key regulatory enzyme that acts to promote ATP-generating pathways such as fatty acid oxidation and inhibits energy storage pathways such as fatty acid synthesis.

Fatty acid oxidation was measured in hepatocytes isolated from livers of ISIS 327895-treated mice. Primary hepatocytes were isolated from lean C57Bl/6 mice treated with saline, ISIS 327895, or ISIS 342683, at 25 mg/kg, twice per week, for a total of 5 doses. Hepatocytes were plated in 25 cm$^2$ culture flasks, at a density of 1×10$^6$ cells per flask. Prior to plating of the cells, the flasks were treated with 2 ml of 0.1 mg/ml collagen in phosphate-buffered saline for 10 minutes at room temperature. Each liver yielded 4 flasks, 3 of which were used for fatty acid oxidation experiments and one of which was reserved for protein measurements. To each flask of hepatocytes was added 3 ml of William E culture medium, supplemented with 1.0 nM insulin and 10% fetal bovine serum (medium and supplements available from, for example, Invitrogen Life Technologies, Carlsbad, Calif.). Following overnight culture, the cells were washed twice with phosphate-buffered saline and were then cultured in 2.0 ml of low-glucose DMEM containing 0.25% bovine serum albumin and 0.25 uCi $^{14}$C-oleaic acid. The flask was filled with 5% $CO_2$/95%$O_2$ and capped with a septa rubber stop, to which was attached a 0.5 ml tube with a filter paper. Three hours lated, 0.4 ml of 70% $HClO_4$ was injected into the culture medium and 0.05 ml of 25% NaOH was immediated injected onto the filter paper to collect the $CO_2$. After 34 hours of $CO_2$ collection, the filter paper was removed and placed in a scintillation vial. The 0.5 ml tube that contained the filter paper was washed twice with water and the water was transferred into the scintillation vial. 1.2 ml of the culture medium was collected from each flask and centrifuged, and the supernatant was transferred to an additional scintillation tube. The radioactivity in the $CO_2$ collection and the culture medium supernatant was determined and used to calculate the fatty acid oxidation rate. Fatty acid oxidation rates were normalized by protein levels in each flask.

The results are shown in FIG. 5. Treatment with ISIS 327895 significantly increased fatty acid oxidation, relative to both saline and control oligonucleotide-treated samples. AMPK levels were also examined by western blotting of whole liver extracts of mice treated with ISIS 327895 and compared to saline or control oligomeric compound-treated mice. Total AMPKalpha1 protein level was unchanged in the ISIS 327895-treated mice, but the levels of phosphorylated AMPKalpha1 were increased more than 2.5 times relative to saline-treated mice.

In accordance with the observed reduction in FASN, ACC1 and ACC2 mRNA after miR-122a inhibition, the fatty acid synthesis rate was reduced almost 2-fold in hepatocytes from mice treated with ISIS 327895 relative to hepatocytes from saline-treated mice. The rate of sterol synthesis was also significantly reduced. Sterol synthesis and fatty acid synthesis rates were determined by measuring the incorporation of [$^{14}$C] acetate into sterols and fatty acids, respectively, using methods described in the art (Jiang, et al, 2005 J. Clin. Invest. 115:1030-1038).

Embodiments of the present invention include methods of lowering hepatic fatty acid synthesis and sterol synthesis and methods of increasing hepatic fatty acid oxidation in an animal comprising administering to said animal an antisense compound targeted to miR-122a. In one embodiment, the antisense compound has the nucleobase sequence of SEQ ID NO: 2. In another embodiment, the antisense compound is uniformly comprised of 2'-MOE sugar modifications. In a further embodiment, the antiense compound is ISIS 327895.

Example 11

Effects of miR-122a Antisense Oligonucleotide Treatment in ob/ob Mice

Eight week old ob/ob mice were given an intraperitoneal injection of ISIS 327895 or a control oligonucleotide dissolved in saline at a dose of 25 mg/kg twice a week for 4.5 weeks. Blood was collected and analyzed using routine clinical analyzer instruments (for example, an Olympus AU400e automated clinical chemistry analyzer, Melville, N.Y.). Treatment with ISIS 327895 caused significant decrease in plasma cholesterol levels (about 168 mg/dL) as compared to treatment with control oligonucleotide (about 237 mg/dL) or saline-treatment alone (about 241 mg/dL).

Antisense inhibition of miR-122a also reduced hepatic triglyceride levels (about 89 mg/g) as compared to treatment with control oligonucleotide (about 161 mg/g) or saline-treatment alone (about 151 mg/g). Liver triglyceride levels are measured using routine methods described in the art (Desai, et al. 2001, Diabetes, 50: 2287-2295. The reduction in steatosis was reflected as a decrease in plasma ALT and AST levels in the group treated with ISIS 327895. Thus, other embodiments of the present invention include methods of decreasing hepatic triglycerides in an animal, methods of decreasing serum cholesterol in an animal, and methods of improving hepatic function in an animal comprising administering an antisense oligonucleotide which inhibits miR-122a function. The present invention also contemplates methods of ameliorating or preventing hyperlipidemia or hepatic steatosis in an animal comprising administering an antisense compound targeted to miR-122a. In one embodiment, the antisense compound has the nucleobase sequence of SEQ ID NO: 2. In another embodiment, the antisense compound is uniformly comprised of 2'-MOE sugar modifications. In a further embodiment, the antiense compound is ISIS 327895.

No change in plasma glucose or glucose tolerance was observed, and no overt toxicities, change in food intake or body weight were observed across treatment groups. These results demonstrate that miR-122a plays a role in regulating cholesterol and lipid metabolism. The effects are independent of leptin action, and there are no overt side effects caused by reduction of miR-122a.

Another embodiment of the present invention is a method of regulating cholesterol and lipid metabolism by inhibiting miR-122a.

Example 12

Antisense Inhibition of miR-122a Activity In Vivo Using Enhanced Antisense Compounds The antisense compounds of the invention modulate the activity or function of the small non-coding RNAs to which they are targeted. In this example, antisense compounds targeted to miR-122a are illustrated; however, the modifications in the antisense compounds of the invention are not limited to those antisense compounds that modulate miR-122a.

Male C57BL/6 mice were obtained from The Jackson Laboratory. Mice were treated with antisense compounds targeting miR-122a, or received saline as a control treatment.

One of the antisense compounds tested included ISIS 327895, a 2'-MOE uniformly modified compound fully complementary to miR-122a. Also tested in vivo was ISIS 387574, a positionally modified antisense compound having the motif (A-A-B)7(-A-A)1 where A is 2'-MOE and B is LNA. ISIS 387574 is fully complementary to miR-122a.

Mice were administered 25 mg/kg doses of antisense compound intraperitoneally, for a total of 6 doses. Following the end of the treatment period, RNA was isolated from liver and the levels of a miR-122a target mRNA, ALDOA, were measured using Taqman real-time PCR. Relative to saline-treated animals, treatment with the 2'-MOE uniformly modified compound resulted in ALDO A mRNA levels approximately 4 times those in saline-treated animals. Treatment with the positionally modified compound resulted in ALDO A miRNA levels approximately 5 times those observed in saline-treated animals. Thus, incorporation of a bicyclic sugar moiety into an otherwise uniformly modified background enhanced the ability of an antisense compound to inhibit miR-122a activity in vivo.

Serum total cholesterol levels were also monitored using methods known in the art (for example, via Olympus AU400e automated clinical chemistry analyzer, Melville, N.Y.). Reductions in total cholesterol were observed in mice treated with either the 2'-MOE uniformly modified compound or the positionally modified 2'-MOE/LNA compound.

Additional measurements performed on serum samples include measurements of LDL-cholesterol, triglycerides, and serum tranaminases. Additional analyses that are performed in such in vivo studies included histological analysis of liver sections, to evaluate changes in morphology. Histological analysis of liver is carried out via routine procedures known in the art. Briefly, liver is fixed in 10% buffered formalin and embedded in paraffin wax. 4-mm sections are cut and mounted on glass slides. After dehydration, the sections are stained with hematoxylin and eosin. Morphological analysis may also include evaluation of hepatic steatosis, using oil Red 0 staining procedures known in the art.

Embodiments of the present invention include methods of reducing serum total cholesterol in an animal comprising administering an antisense compound targeted to a miR-122a nucleic acid. In one embodiment, the antisense compound has the nucleobase sequence of SEQ ID NO: 2. In another embodiment, the antisense compound is uniformly comprised of 2'-MOE sugar modifications. In additional embodiments, the antisense compound has a positionally modified motif, 5'-(A-A-B)n(-A)nn-3', where A is 2'-MOE, B is LNA, n is 7, and nn is 2. In a further embodiment, the antiense compound is ISIS 327895. In another embodiment, the antisense compound is ISIS 387574. Additionally, either of these antisense compounds is used to achieve one or more additional phenotypic changes, such as lowered serum LDL-cholesterol, lowered serum triglycerides, or reduced hepatic steatosis.

In a similar study, antisense compounds targeted to miR-122a and having truncations were tested in vivo. Truncation of a single nucleoside from the 5' end of the antisense compound yielded increases in ALDO A mRNA levels comparable to those of the full-length antisense compound, ISIS 327895. Truncations of two nucleosides from the 5' end, 5 nucleosides from the 3' end, or 1 nucleoside from the 3' end resulted in slightly elevated ALDO A mRNA levels. Truncation of 3 nucleosides from the 3' end resulted in no increase in ALDO A mRNA levels. Accordingly, a further embodiment of the invention includes practicing any of the methods described herein using an antisense compound targeted to miR-122a, wherein the antisense compound has no more than 2 truncations from the 5' end or no more than 1 truncation from the 3' end, relative to the nucleobase sequence of SEQ ID NO: 2.

What is claimed is:

1. A method of lowering serum cholesterol levels in an animal comprising
    a) selecting an animal having elevated serum cholesterol levels; and
    b) administering to the animal a therapeutically effective amount of an antisense compound having at least 90% nucleobase sequence complementarity to a miR-122a nucleic acid, thereby lowering serum cholesterol levels.

2. The method of claim 1, comprising lowering serum LDL-cholesterol.

3. The method of claim 1, wherein the antisense compound is 21 to 23 nucleosides in length.

4. The method of claim 1, wherein the antisense compound is fully complementary to a miR-122a target nucleic acid.

5. The method of claim 3, wherein the antisense compound comprises a plurality of 2'-sugar modified nucleosides.

6. The method of claim 5, wherein the antisense compound further comprises at least one bicyclic sugar modified nucleoside.

7. The method of claim 4, wherein the antisense compound comprises the nucleobase sequence of SEQ ID NO: 1.

8. The method of claim 7, wherein the antisense compound consists of the nucleobase sequence of SEQ ID NO: 2.

9. The method of claim 8, wherein the antisense compound is uniformly comprised of 2'-MOE sugar modified nucleosides.

10. The method of claim 9, wherein the antisense compound comprises at least one phosphorothioate internucleoside linkage.

11. The method of claim 9, wherein the antisense compound comprises at least one 5-methylcytosine.

12. The method of claim 1, wherein the antisense compound is an antisense oligonucleotide.

13. The method of claim 1, wherein the antisense compound is an antisense oligonucleotide 15 to 30 linked nucleosides in length.

14. The method of claim 1, wherein the antisense compound is an antisense oligonucleotide 17 to 25 linked nucleosides in length.

15. The method of claim 1, wherein the animal has a disease or disorder selected from diabetes, obesity, hyperlipidemia, hypercholesterolemia, hypertriglyceridemia, hyperfattyacidemia, nonalcoholic fatty liver disease, non alcoholic steatohepatitis, and metabolic syndrome.

16. The method of claim 1, wherein the antisense compound comprises at least one bicyclic sugar modification.

17. The method of claim 16, wherein the bicyclic sugar modification is LNA.

18. The method of claim 1, wherein the animal is a human.

19. A method comprising administering to an animal having elevated serum cholesterol an antisense compound having at least 90% nucleobase sequence complementarity to a miR-122a nucleic acid, thereby lowering serum cholesterol in the animal.

20. The method of claim 19, wherein the antisense compound is 15 to 30 nucleosides in length.

21. The method of claim 19, wherein the antisense compound is 21 to 23 nucleosides in length.

22. The method of claim 19, wherein the antisense compound is 17 to 25 nucleosides in length.

23. The method of claim 19, wherein the antisense compound is fully complementary to a miR-122a target nucleic acid.

24. The method of claim 19, wherein the antisense compound comprises a plurality of 2'-sugar modified nucleosides.

25. The method of claim 19, wherein the antisense compound comprises at least one bicyclic sugar modification.

26. The method of claim 25, wherein the bicyclic sugar modification is LNA.

27. The method of claim 19, wherein the antisense compound comprises the nucleobase sequence of SEQ ID NO: 1.

28. The method of claim 19, wherein the antisense compound consists of the nucleobase sequence of SEQ ID NO: 2.

29. The method of claim 19, wherein the antisense compound is uniformly comprised of 2'-MOE sugar modified nucleosides.

30. The method of claim 19, wherein the antisense compound comprises at least one phosphorothioate internucleoside linkage.

31. The method of claim 19, wherein the antisense compound comprises at least one 5-methylcytosine.

32. The method of claim 19, wherein the antisense compound is an antisense oligonucleotide.

33. The method of claim 19, wherein the animal is a human.

34. The method of claim 12, wherein the antisense oligonucleotide consists of the nucleobase sequence of SEQ ID NO:2, each nucleoside is a 2'—O-methoxyethyl nucleoside, each linkage is a phosphorothioate linkage, and each cytosine is a 5-methyl cytosine.

35. The method of claim 32, wherein the antisense oligonucleotide consists of the nucleobase sequence of SEQ ID NO:2, each nucleoside is a 2'—O-methoxyethyl nucleoside, each linkage is a phosphorothioate linkage, and each cytosine is a 5-methyl cytosine.

36. The method of claim 4, wherein the miR-122a nucleic acid comprises SEQ ID NO:3.

37. The method of claim 23, wherein the miR-122a nucleic acid comprises SEQ ID NO:3.

\* \* \* \* \*